United States Patent
Morgan et al.

(10) Patent No.: US 12,065,395 B2
(45) Date of Patent: Aug. 20, 2024

(54) PROCESSES FOR THE PREPARATION OF DEUTERATED D-SERINE

(71) Applicant: Sun Pharmaceutical Industries, Inc., Princeton, NJ (US)

(72) Inventors: Adam Morgan, Ashland, MA (US); Robert S. Lewis, Lexington, MA (US)

(73) Assignee: Sun Pharmaceutical Industries, Inc., Princeton, NJ (US)

( * ) Notice: Subject to any disclaimer, the term of this patent is extended or adjusted under 35 U.S.C. 154(b) by 67 days.

(21) Appl. No.: 17/601,348

(22) PCT Filed: Apr. 3, 2020

(86) PCT No.: PCT/US2020/026739
§ 371 (c)(1),
(2) Date: Oct. 4, 2021

(87) PCT Pub. No.: WO2020/206367
PCT Pub. Date: Oct. 8, 2020

(65) Prior Publication Data
US 2022/0169595 A1    Jun. 2, 2022

Related U.S. Application Data

(60) Provisional application No. 62/828,884, filed on Apr. 3, 2019.

(51) Int. Cl.
C07C 227/32    (2006.01)
C07D 263/04    (2006.01)

(52) U.S. Cl.
CPC .......... *C07C 227/32* (2013.01); *C07D 263/04* (2013.01)

(58) Field of Classification Search
None
See application file for complete search history.

(56) References Cited

U.S. PATENT DOCUMENTS

| 4,582,931 A | 4/1986 | Grabowski et al. |
|---|---|---|
| 6,221,335 B1 | 4/2001 | Foster |
| 6,440,710 B1 | 8/2002 | Keinan et al. |
| 6,603,008 B1 | 8/2003 | Ando et al. |
| 7,517,990 B2 | 4/2009 | Ito et al. |
| 10,668,036 B2 | 6/2020 | Doller et al. |
| 2007/0082929 A1 | 4/2007 | Gant et al. |
| 2007/0197695 A1 | 8/2007 | Potyen et al. |
| 2008/0103122 A1 | 5/2008 | Veltri |

FOREIGN PATENT DOCUMENTS

| WO | WO 1995/26325 | 10/1995 |
|---|---|---|
| WO | WO 2007/118651 | 10/2007 |
| WO | WO 2019/104179 | 5/2019 |

OTHER PUBLICATIONS

Seebach ("107. Stereoselective Alkylierung an C(α) von Serin, Glycerinsäure, Threonin und Weinsäure über heterocyclishe Enolate mit exocyclishcher Doppelbindung" Helv. Chim. Acta. (70), 1987, p. 1194-1216) (Year: 1987).*

(Continued)

*Primary Examiner* — Amy C Bonaparte
(74) *Attorney, Agent, or Firm* — Fish & Richardson P.C.

(57) ABSTRACT

Disclosed are methods for preparing deuterated analogs of D-serine and compounds useful for preparing deuterated analogs of D-serine.

21 Claims, 1 Drawing Sheet

(56) References Cited

OTHER PUBLICATIONS

Brunner ("Stereocontrolled α-Alkylation of Fully Protected L-Serine" Eur. J. Org. Chem. 2004, p. 3879-3883) (Year: 2004).*
Greene ("N-Benzylamine" Greene's Protective Groups in Organic Synthesis, 2007, p. 814-818) (Year: 2007).*
Anson, M.S. et al., Org. Process Res. Dev., "Complementary Syntheses of N,O-Protected-(S)-2-methylserine on a Multikilogram Scale," 2011, 15:389-397.
Baillie, T. A., "The Use of Stable Isotopes in Pharmacological Research," Pharmacological Reviews, 33(2): 81-132 (1981).
Blake et al., "Studies with Deuterated Drugs," J Pharm Sci, 1975, 64:367-391.
Browne, T. R., "Stable Isotope Techniques in Early Drug Development: An Economic Evaluation," J. Clin. Pharmacol., 38: 213-220 (1998).
Cherrah, Y., et al., "Study of Deuterium Isotope Effects on Protein Binding by Gas Chromatography/Mass Spectrometry. Caffeine and Deuterated Isotopomers," Biomedical and Environmental Mass Spectrometry, 14: 653-657 (1987).
Dyck, L. E., et al., "Effects of Deuterium Substitution on the Catabolism of β-Phenylethylamine: An In Vivo Study," Journal of Neurochemistry, 46(2): 399-404 (1986).
Fisher, M.B. et al., "The Complexities Inherent in Attempts to Decrease Drug Clearance by Blocking Sites of CYP-Mediated Metabolism," Curr. Opin. Drug Discov. Devel., 9(1):101-109 (2006).
Foster, A. B., "Deuterium Isotope Effects in Studies of Drug Metabolism," Trends in Pharmacological Sciences, 5: 524-527 (1984).
Foster, A. B., "Deuterium Isotope Effects in the Metabolism of Drugs and Xenobiotics: Implications for Drug Design," Advances in Drug Research, 14: 1-40 (1985).
Fukuto, et al., Determination of the Mechanism of Demethylenation of (Methylenedioxy) phenyl Compounds by Cytochrome P450 Using Deuterium Isotope Effects, J Med Chem, 1991, 34:2871-2876.
Gouyette, A., "Synthesis of Deuterium-labelled Elliptinium and its Use in Metabolic Studies," Biomedical and Environmental Mass Spectrometry, 15: 243-247 (1988).
Hashimoto, A. et al.: "Effect of systemic administration of D-serine on the levels of D- and L-serine in several areas and periphery of rat", European Jpournal of Pharmacology, vol. 495, No. 2-3, Jul. 14, 2004 (Jul. 14, 2004), pp. 153-158. 10.1016/j.ejphar.2004.050.36.
Haskins, N. J., "The Application of Stable Isotopes in Biomedical Research," Biomedical Mass Spectrometry, 9(7): 269-277 (1982).
Honma S., et al., "The Metabolism of Roxatidine Acetate Hydrochloride," Drug Metabolism and Disposition, 15(4): 551-559 (1987).
Lio, Y. et al., "Asymmetric Synthesis of a,apDisubstituted a-Amino Alcohol Derivatives," Tet. Asymm. 22:323-328 (2011).
International Preliminary Report on Patentability in Appln. No. PCT/US2020/026739, dated Sep. 28, 2021, 9 pages.
International Search Report and Written Opinion in Appln. No. PCT/US2020/26739, dated Jun. 19, 2020, 11 pages.
Kushner, D.J. et al., "Pharmacological Uses and Perspectives of Heavy Water and Deuterated Compounds," Can. J. Physiol. Pharmacol., 77:79-88 (1999).
Loh, T-P et al.: "Synthetic Studies Towards Kaitocephalin", Tetrahedron Letters, 42:7893-7897, 2001.
Pieniaszek, H. J., et al., "Moricizine Bioavailability via Simultaneous, Dual, Stable Isotope Administration: Bioequivalence Implications," J. Clin. Pharmacol, 39: 817-825 (1999).
Reider, P.J., et al., "Synthesis of (R)-Serine-2-d and Its Conversion to the Broad Spectrum Antibiotic Fludalanine," J. Org. Chem. 52:3326-3334 (1987).
Seebach, D., Aebi, J.D., "Alpha-Alkylation of Serine With Self-Reproduction of the Center of Chirality," Tet. Lett.25 (24):2545-2548 (1984).
Tonn G. R., et al., "Simultaneous Analysis of Diphenhydramine and a Stable Isotope Analog ($^2H_{10}$) Diphenhydramine Using Capillary Gas Chromatography with Mass Selective Detection in Biological Fluids from Chronically Instrumented Pregnant Ewes," Biological Mass Spectrometry, 22: 633-642 (1993).
Wolen, R. L., "The Application of Stable Isotopes to Studies of Drug Bioavailability and Bioequivalence," J. Clin. Pharmacol., 26: 419-424 (1986).

* cited by examiner

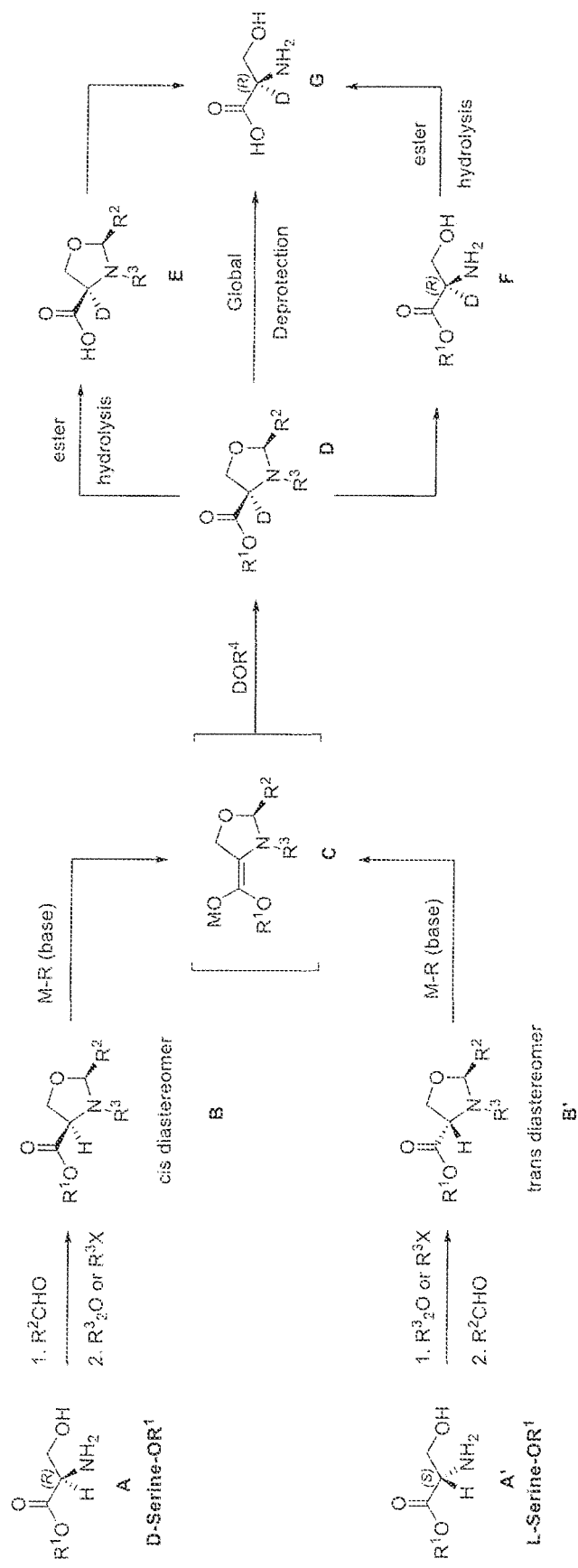

PROCESSES FOR THE PREPARATION OF DEUTERATED D-SERINE

RELATED APPLICATIONS

This application is a national phase entry under 35 U.S.C. § 371 of International Application No. PCT/US2020/026739, filed on Apr. 2, 2020, and claims the benefit of and priority to U.S. Provisional Patent Application No. 62/828,884, filed Apr. 3, 2019, the contents of which are incorporated herein by reference in their entirety.

BACKGROUND OF THE INVENTION

D-Serine occurs naturally in the human body, although in much smaller amounts than L-serine. Only L-serine is found in proteins.

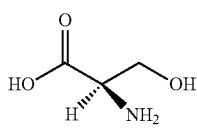

(D-Serine)

D-Serine is an agonist of NMDA receptors. Academic studies have demonstrated that oral dosing of D-serine can result in dose-dependent improvement in positive, negative, and cognitive symptoms in schizophrenic patients when added to D2 antipsychotics (antipsychotic drugs that bind to and inhibit or block the activation of dopamine D2 receptors). However, preclinical studies have demonstrated that administration of D-serine can cause nephrotoxicity in rats. In addition, in some patients who received high doses of D-serine, clinical findings suggesting renal impairment were observed. As a result, the clinical development of D-serine has historically been limited.

Deuterated analogs of D-serine have recently been reported to have lower nephrotoxicity than D-serine in preclinical studies in rats. Although methods for producing deuterated forms of D-serine have been reported, these methods often require the use of large quantities of expensive deuterated reagents, have low yields, or require separation of the unwanted L-serine enantiomer. Improved methods for producing deuterated analogs of D-serine are therefore needed.

SUMMARY OF THE INVENTION

It has now been found that deuterated forms of D-serine can be prepared from D-serine with improved yields and reduced costs.

In one aspect, this invention relates to a method for preparing deuterated forms of D-serine, such as D-serine-2-d.

In one aspect, the invention provides a method for preparing D-serine-2-d,

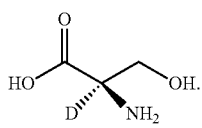

(D-serine-2-d)

The method comprises:
contacting a compound of Formula E;

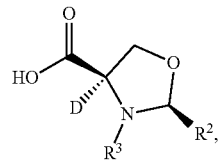

(E)

wherein
$R^2$ is $C_1$-$C_6$alkyl, $C_3$-$C_6$cycloalkyl, or aryl; and
$R^3$ is H, D, or a protecting group,
with acid under conditions such that D-serine-2-d is formed;
wherein the D-serine-2-d has a deuterium incorporation of at least 90% at the position specified as deuterium.

In certain embodiments, the compound of Formula E, $R^2$ is $C_1$-$C_6$alkyl. In certain embodiments, $R^2$ is isopropyl or t-butyl. In certain embodiments, $R^3$ is a protecting group. In certain embodiments, $R^3$ is a protecting group selected from —C(O)H, —C(O)—X—$C_1$-$C_6$alkyl, —C(O)—X—$C_3$-$C_6$cycloalkyl, —C(O)—X—$CH_2$-aryl, —C(O)—X-aryl, —$CH_2$-aryl, wherein X is absent, O, NH, or S. In certain embodiments, the compound of Formula E is selected from the group consisting of:

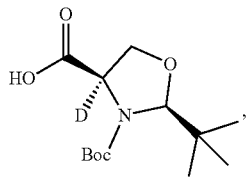

(50)

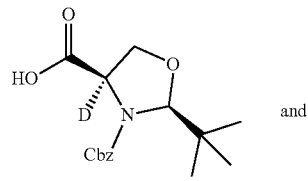

(50c)

and

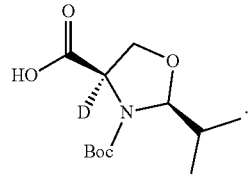

(50d)

In certain embodiments, the method further comprises, prior to the step of contacting the compound of Formula E with an acid, the steps of:

(i) contacting a compound of Formula B:

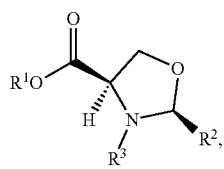

(B)

wherein

R₁ is H, $C_1$-$C_6$alkyl, $C_3$-$C_6$cycloalkyl, —$CH_2$-aryl, or aryl;

$R^2$ is $C_1$-$C_6$alkyl, $C_3$-$C_6$cycloalkyl, or aryl; and $R^3$ is H, D, or a protecting group, with a base to form a first reaction mixture;

(ii) contacting the first reaction mixture with a deuterium source to form a second reaction mixture; and (iii) contacting the second reaction mixture with a base to form the compound of Formula E.

In certain embodiments, the acid is HCl.

In one aspect, the invention provides a method for preparing compound 40a,

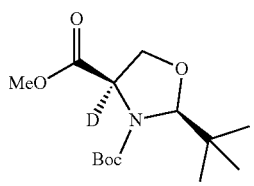

(40a)

the method comprising the steps of:

contacting compound 30a

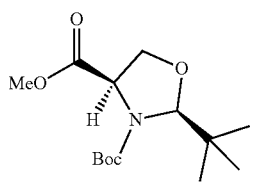

(30a)

with a base to form a reaction mixture; and contacting the reaction mixture with 1-10 equivalents of a deuterium source; under conditions such that compound 40a is formed;

wherein the compound 40a has a deuterium incorporation of at least 90% at the position specified as deuterium.

In another aspect, the invention provides a method for preparing compound 50,

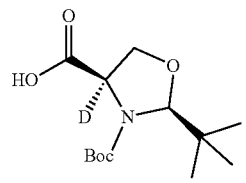

(50)

the method comprising the steps of:

(i) contacting compound 30a

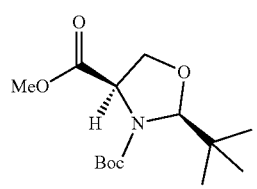

(30a)

with a base to form a reaction mixture;

(ii) contacting the reaction mixture with a deuterium source;

under conditions such that compound 40a is formed:

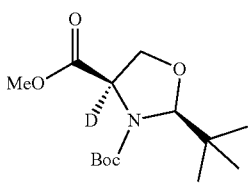

(40a)

and (iii) reacting compound 40a with a base to form compound 50;

wherein the compound 50 has a deuterium incorporation of at least 90% at the position specified as deuterium.

In another aspect, the invention provides a compound represented by the structure (D):

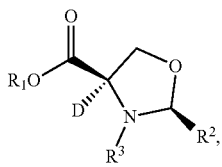

(D)

wherein, $R^1$ is H, $C_1$-$C_6$alkyl, $C_3$-$C_6$cycloalkyl, —$CH_2$-aryl, or aryl;

$R^2$ is $C_1$-$C_6$alkyl, $C_3$-$C_6$cycloalkyl, or aryl;

$R^3$ is H, D, or a protecting group; and wherein the compound has a deuterium incorporation of at least 90% at the position specified as deuterium.

In another aspect, the invention provides a compound represented by the structure (E):

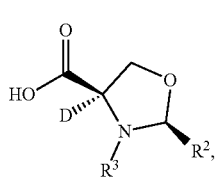
(E)

wherein,
$R^2$ is $C_1$-$C_6$alkyl, $C_3$-$C_6$cycloalkyl, or aryl;
$R^3$ is H, D, —C(O)—X—$C_1$-$C_6$alkyl, —C(O)—X—$C_3$-$C_6$cycloalkyl, —C(O)—X-aryl, wherein X is absent, O, NH, or S; and
wherein the compound has a deuterium incorporation of at least 90% at the position specified as deuterium.

In another aspect, the invention provides a method for preparing compound 40a:

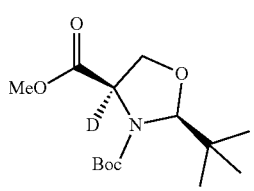
(40a)

the method comprising the steps of:
contacting compound 30'

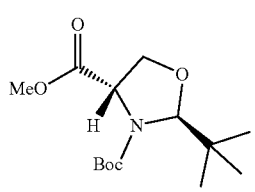
(30a')

with a base to form a reaction mixture; and
contacting the reaction mixture with 1-10 equivalents of a deuterium source;
under conditions such that compound 40a is formed;
wherein the compound 40a has a deuterium incorporation of at least 90% at the position specified as deuterium.

In another aspect, the invention provides a method for preparing compound 40a:

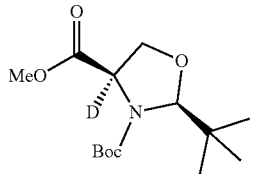
(40a)

the method comprising the steps of:
contacting compound 30a"

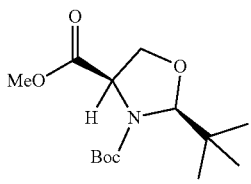
(30a")

with a base to form a reaction mixture; and
contacting the reaction mixture with 1-10 equivalents of a deuterium source;
under conditions such that compound 40 is formed;
wherein the compound 40 has a deuterium incorporation of at least 90% at the position specified as deuterium.

In another aspect, the invention provides a method for preparing D-serine-2-d, the method comprising the steps of:
(i) contacting compound 30a

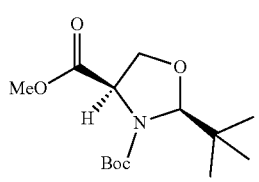
(30a)

with a base to form a reaction mixture; and
(ii) contacting the reaction mixture with 1-10 equivalents of a deuterium source;
under conditions such that compound 40a is formed

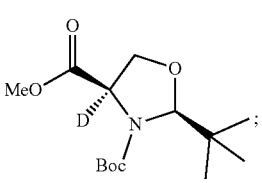
(40a)

(iii) contacting compound 40a with a base under conditions such that compound 50 is formed

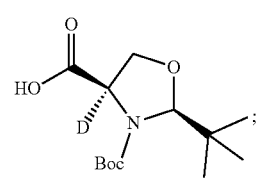
(50)

and
(iv) contacting compound 50 with acid under conditions such that D-serine-2-d is formed;
wherein the D-serine-2-d has a deuterium incorporation of at least 90% at the position specified as deuterium.

In certain embodiments, the base in step (i) is mesityllithium. In certain embodiments, the base in step (iii) is lithium deuteroxide. In certain embodiments, the acid in step (iv) is HCl.

In another aspect, the invention provides method for preparing compound 50,

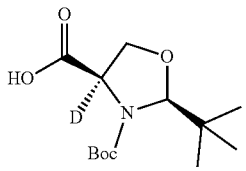
(50)

the method comprising the steps of.
reacting compound 40a

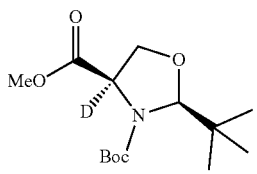
(40a)

with 1-10 equivalents of lithium deuteroxide to form compound 50.

In certain embodiments, the compound 50 has a deuterium incorporation of at least 90% at the position specified as deuterium.

In certain embodiments, the method comprises preparing D-serine-2-d according to the methods described herein, and formulating D-serine-2-d with one or more pharmaceutical excipients, to provide a pharmaceutical composition comprising D-serine-2-d. In certain embodiments the method comprises preparing D-serine-2-d according to the methods described herein, and mixing D-serine-2-d with a pharmaceutically acceptable carrier, to form the pharmaceutical composition.

Further aspects and embodiments of the invention are also disclosed herein.

BRIEF DESCRIPTION OF THE DRAWINGS

The FIGURE shows a general scheme for the preparation of D-serine-2-d.

DETAILED DESCRIPTION OF THE INVENTION

The present invention relates to methods for preparing deuterated analogs of D-serine and to compounds useful for preparing deuterated analogs of D-serine.

In one aspect, the invention provides a method for preparing D-serine-2-d,

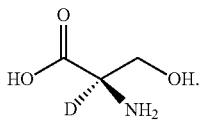
(D-serine-2-d)

The method comprises:
contacting a compound of Formula E;

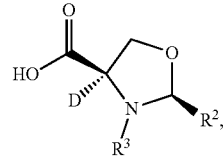
(E)

wherein
R$^2$ is C$_1$-C$_6$alkyl, C$_3$-C$_6$cycloalkyl, or aryl; and
R$^3$ is H, D, or a protecting group,
with acid under conditions such that D-serine-2-d is formed;
wherein the D-serine-2-d has a deuterium incorporation of at least 90% at the position specified as deuterium.

In certain embodiments, the compound of Formula E, R$^2$ is C$_1$-C$_6$alkyl. In certain embodiments, R$^2$ is isopropyl or t-butyl. In certain embodiments, R$^3$ is a protecting group. In certain embodiments, R$^3$ is a protecting group selected from —C(O)H, —C(O)—X—C1-C6alkyl, —C(O)—X—C$_3$-C$_6$cycloalkyl, —C(O)—X—CH$_2$-aryl, —C(O)—X-aryl, —CH$_2$-aryl, wherein X is absent, O, NH, or S. In certain embodiments, the compound of Formula E is selected from the group consisting of:

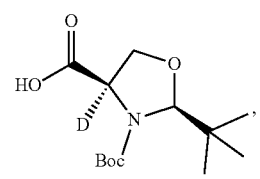
(50)

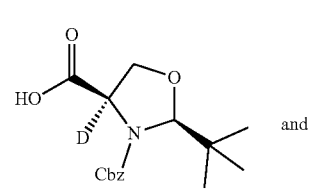
(50c)
and

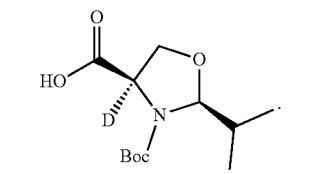
(50d)

In certain embodiments, the method further comprises, prior to the step of contacting the compound of Formula E with an acid, the steps of:
(iv) contacting a compound of Formula B:

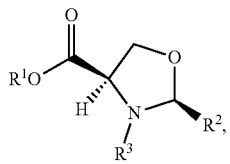
(B)

wherein

R₁ is H, $C_1$-$C_6$alkyl, $C_3$-$C_6$cycloalkyl, —$CH_2$-aryl, or aryl;

R² is $C_1$-$C_6$alkyl, $C_3$-$C_6$cycloalkyl, or aryl; and

R³ is H, D, or a protecting group, with a base to form a first reaction mixture;

(v) contacting the first reaction mixture with a deuterium source to form a second reaction mixture; and (vi) contacting the second reaction mixture with a base to form the compound of Formula E.

In certain embodiments, the acid is HCl.

In one aspect, the invention provides a method for preparing compound 40a,

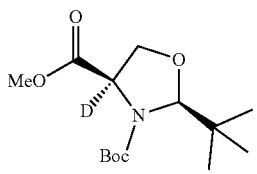

(40a)

the method comprising the steps of:

contacting compound 30a

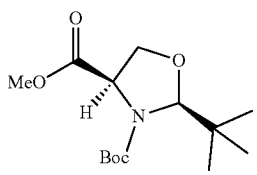

(30a)

with a base to form a reaction mixture; and contacting the reaction mixture with at least 1 equivalent of a deuterium source;

under conditions such that compound 40a is formed;

wherein the compound 40a has a deuterium incorporation of at least 90% at the position specified as deuterium.

In certain embodiments of the above aspect, the base is any base wherein the pKa of the conjugate acid of the base is about 30 or greater, as measured in DMSO. In certain embodiments, the pKa of the conjugate acid of the base is at least 30.

In certain embodiments of the above aspect, the base is represented by Formula MR$^x$, wherein, M is selected from Li, Na, Mg and K;

R$^x$ is selected from phenyl, substituted phenyl, $C_1$-$C_6$ alkyl optionally substituted, and N(R$^Y$)₂; wherein R$^Y$ is $C_1$-$C_6$ alkyl or Si(CH₃)₃.

In certain embodiments of the base represented by Formula MR$^x$, M is Na or Li. In certain embodiments, M is Na. In certain embodiments, M is Li.

In certain embodiments of the above aspect, the base is represented by Formula I,

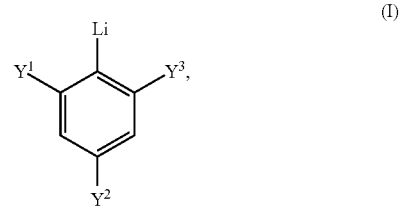

(I)

wherein each of Y¹, Y² and Y³ is independently selected from H, $C_1$-$C_6$ alkyl, —OY⁴, and —N(Y⁵)₂; Y⁴, if present, is $C_1$-$C_6$ alkyl, —$CH_2OCH_3$, or —$CH_2OCH_2$phenyl; and Y⁵, if present, is $C_1$-$C_6$ alkyl. In certain embodiments, each of Y¹, Y² and Y³ is independently selected from H, —CH₃, and —OCH₃. In certain embodiments, Y¹, Y² and Y³ are the same.

In certain embodiments, the base is selected from mesityllithium, 2,6-dimethoxyphenyllithium, 2,4,6-trimethoxyphenyllithium, tolyllithium, t-butyllithium, phenyllithium, lithium hexamethyldisilazide (LHMDS), trityllithium, phenylsodium and tritylsodium. In certain embodiments, the base is mesityllithium. In certain embodiments, the base is 2,6-dimethoxyphenyllithium. In certain embodiments, the base is 2,4,6-trimethoxyphenyllithium. In certain embodiments, contacting the reaction mixture with a deuterium source, comprises using 1-10 equivalents of the deuterium source. In certain embodiments, the deuterium source is D₂O. In certain embodiments, the deuterium source is $CH_3CO_2D$ (DOAc).

In certain embodiments, the step of contacting compound 30a with the base to form the reaction mixture occurs at a temperature in the range from −100° C. to −50° C. In certain embodiments the temperature is a temperature in the range from about −90° C. to about −60° C. In certain embodiments the temperature is a temperature in the range from about −80° C. to about −60° C.

In certain embodiments, the step of contacting compound 30a with the base to form the reaction mixture occurs in an aprotic solvent. In specific embodiments, the aprotic solvent is THF, hexanes or heptane, or a mixture thereof.

In certain embodiments, compound 30a is contacted with the base to form the reaction mixture for a time in the range from 5 minutes to 2 hours. In certain embodiments, the time is a time in the range from 30 minutes to 2 hours. In certain specific embodiments, the time is about 30 minutes. In certain specific embodiments, the time is about 60 minutes.

In certain embodiments, the step of contacting compound 30a with the base to form the reaction mixture under an inert atmosphere.

In certain embodiments, the reaction mixture is contacted with less than 10 equivalents of the deuterium source (i.e., less than 10 moles of deuterium source per mole of Compound 30a). In more specific embodiments, the reaction mixture is contacted with less than 5 equivalents of the deuterium source. In certain specific embodiments, the reaction mixture is contacted with 3 to 4 equivalents of the deuterium source. In certain specific embodiments, the reaction mixture is contacted with 1 to 2 equivalents of the deuterium source. In certain specific embodiments, the reaction mixture is contacted with 3 equivalents of the deuterium source. In certain specific embodiments, the reaction mixture is contacted with 4 equivalents of the deuterium source.

In certain embodiments, compound 40a is not isolated.

In one aspect, the invention provides a method for preparing compound 40b,

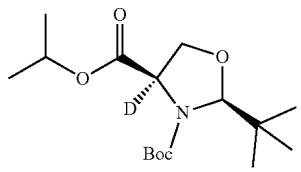

(40b)

the method comprising the steps of:
contacting compound 30b

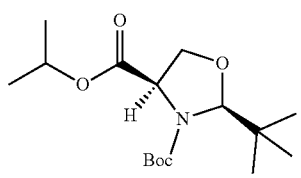

(30b)

with a base to form a reaction mixture; and
contacting the reaction mixture with 1-10 equivalents of a deuterium source;
under conditions such that compound 40b is formed;
wherein the compound 40b has a deuterium incorporation of at least 90% at the position specified as deuterium.
In certain embodiments of the above aspect, the base is represented by Formula I,

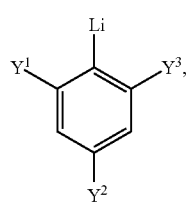

(I)

wherein each of $Y^1$, $Y^2$ and $Y^3$ is independently selected from H, $C_1$-$C_6$ alkyl, —$OY^4$, and —$N(Y^5)_2$; $Y^4$, if present, is $C_1$-$C_6$ alkyl, —$CH_2OCH_3$, or —$CH_2OCH_2$phenyl; and $Y^5$, if present, is $C_1$-$C_6$ alkyl. In certain embodiments, each of $Y^1$, $Y^2$ and $Y^3$ is independently selected from H, —$CH_3$, and —$OCH_3$.

In certain embodiments, $Y^1$, $Y^2$ and $Y^3$ are the same.

In certain embodiments of the above aspect, the base is selected from mesityllithium, 2,6-dimethoxyphenyllithium, 2,4,6-trimethoxyphenyllithium, tolyllithium, t-butyllithium, phenyllithium, lithium hexamethyldisilazide (LHMDS), trityllithium, phenylsodium and tritylsodium. In certain embodiments, the base is tolyllithium. In certain embodiments, the base is 2,6-dimethoxyphenyllithium. In certain embodiments, the base is 2,4,6-trimethoxyphenyllithium. In certain embodiments, the deuterium source is $D_2O$. In certain embodiments, the deuterium source is $CH_3CO_2D$ (DOAc).

In certain embodiments, the step of contacting compound 30b with the base to form the reaction mixture occurs at a temperature in the range from −100° C. to −50° C. In certain embodiments the temperature is a temperature in the range from about −90° C. to about −60° C. In certain embodiments the temperature is a temperature in the range from about −80° C. to about −60° C.

In certain embodiments, the step of contacting compound 30b with the base to form the reaction mixture occurs in an aprotic solvent. In specific embodiments, the aprotic solvent is THF, hexanes or heptane, or a mixture thereof.

In certain embodiments, compound 30b is contacted with the base to form the reaction mixture for a time in the range from 5 minutes to 2 hours. In certain embodiments, the time is a time in the range from 30 minutes to 2 hours. In certain specific embodiments, the time is about 30 minutes. In certain specific embodiments, the time is about 60 minutes.

In certain embodiments, the step of contacting compound 30b with the base to form the reaction mixture occurs under an inert atmosphere.

In certain embodiments, the reaction mixture is contacted with less than 10 equivalents of the deuterium source (i.e., less than 10 moles of deuterium source per mole of Compound 30b). In more specific embodiments, the reaction mixture is contacted with less than 5 equivalents of the deuterium source. In certain specific embodiments, the reaction mixture is contacted with 3 to 4 equivalents of the deuterium source. In certain specific embodiments, the reaction mixture is contacted with 1 to 2 equivalents of the deuterium source. In certain specific embodiments, the reaction mixture is contacted with 3 equivalents of the deuterium source. In certain specific embodiments, the reaction mixture is contacted with 4 equivalents of the deuterium source.

In certain embodiments, compound 40a is not isolated.

In another aspect, the invention provides a method for preparing compound 50,

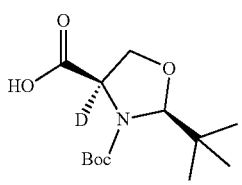

(50)

the method comprising the steps of:
(i) contacting compound 30a

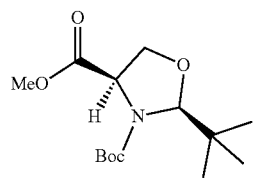

(30a)

with a base to form a reaction mixture;
(ii) contacting the reaction mixture with a deuterium source;

under conditions such that compound 40a is formed:

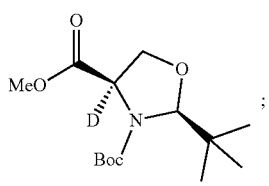
(40a)

and (iii) reacting compound 40a with a base to form compound 50;

wherein the compound 50 has a deuterium incorporation of at least 90% at the position specified as deuterium.

In certain embodiments, the base in step (i) is mesityllithium. In certain embodiments, the base in step (i) is 2,6-dimethoxyphenyllithium. In certain embodiments, the base in step (i) is 2,4,6-trimethoxyphenyllithium. In certain embodiments, the base in step (iii) is a deuteroxide. In certain embodiments, the base in step (iii) is selected from LiOD, NaOD, KOD and Mg(OD)$_2$. In certain embodiments, the base in step (iii) is LiOD. In certain embodiments, compound 50 is formed without isolation of compound 40a.

In another aspect, the invention provides a method for preparing compound 50,

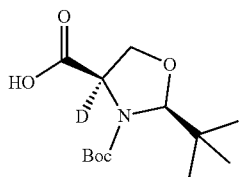
(50)

the method comprising the steps of:
a) contacting compound 30b

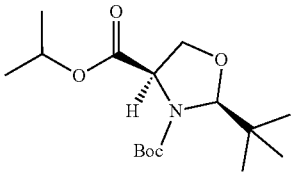
(30b)

with a base to form a reaction mixture;
b) contacting the reaction mixture with a deuterium source;
under conditions such that compound 40b is formed:

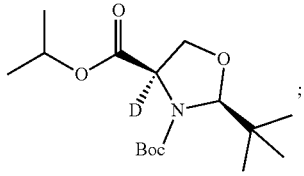
(40b)

and c) reacting compound 40b with a base to form compound 50;

wherein the compound 50 has a deuterium incorporation of at least 90% at the position specified as deuterium.

In certain embodiments, the base in step (a) is tolyllithium. In certain embodiments, the base in step (a) is 2,6-dimethoxyphenyllithium. In certain embodiments, the base in step (a) is 2,4,6-trimethoxyphenyllithium. In certain embodiments, the base in step (c) is a deuteroxide. In certain embodiments, the base in step (c) is selected from LiOD, NaOD, KOD and Mg(OD)$_2$. In certain embodiments, the base in step (c) is LiOD. In certain embodiments, compound 50 is formed without isolation of compound 40b.

In one aspect, the invention provides a method for preparing D-serine-2-d, the method comprising the steps of:

contacting compound 30a

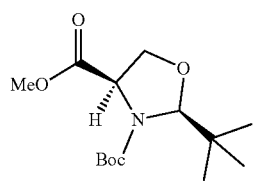
(30a)

with a base to form a reaction mixture; and contacting the reaction mixture with 1-10 equivalents of a deuterium source;

under conditions such that compound 40a is formed

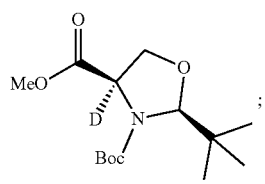
(40a)

contacting compound 40a with a base under conditions such that compound 50 is formed

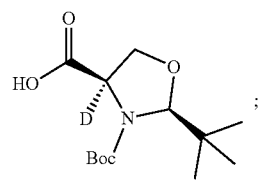
(50)

and contacting compound 50 with acid under conditions such that D-serine-2-d is formed; wherein the D-serine-2-d has a deuterium incorporation of at least 90% at the position specified as deuterium.

In another aspect, the invention provides a compound represented by the structure (D):

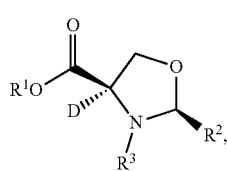
(D)

wherein
R$^1$ is H, C$_1$-C$_6$alkyl, C$_3$-C$_6$cycloalkyl, —CH$_2$-aryl, or aryl;
R$^2$ is C$_1$-C$_6$alkyl, C$_3$-C$_6$cycloalkyl, or aryl; and
R$^3$ is H, D, or a protecting group;
wherein the compound has a deuterium incorporation of at least 90% at the position specified as deuterium.

In certain embodiments, R$^1$ is H, methyl, ethyl, isopropyl, t-butyl, isobutyl, neopentyl or benzyl.

In certain embodiments, R$^2$ is isopropyl, t-butyl, isobutyl or phenyl.

In certain embodiments, R$^3$ is H. In certain embodiments, the protecting group is —C(O)H, —C(O)—X—C$_1$-C$_6$alkyl, —C(O)—X—C$_3$-C$_6$cycloalkyl, —C(O)—X—CH$_2$-aryl, —C(O)—X-aryl, —S(O$_2$)—C$_1$-C$_6$alkyl, or S(O$_2$)-aryl, wherein X is absent, O or NR$^5$, wherein R$^5$ is C$_1$-C$_6$alkyl.

In certain embodiments, R$^3$ is H. In certain embodiments, R$^3$ is a protecting group wherein the protecting group is —C(O)H, —C(O)—X—C$_1$-C$_6$alkyl, —C(O)—X—C$_3$-C$_6$cycloalkyl, —C(O)—X—CH$_2$-aryl, —C(O)—X-aryl, —CH$_2$-aryl, —S(O$_2$)—C$_1$-C$_6$alkyl, or S(O$_2$)-aryl, wherein X is absent, O or NR$^5$, wherein R$^5$ is H or C$_1$-C$_6$alkyl. In certain examples, R$^3$ is t-butyloxycarbonyl (Boc), benzyl, benzyloxycarbonyl (Cbz), formyl or methoxycarbonyl (Moc).

In another aspect, the invention provides a compound represented by the structure (E):

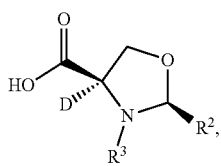
(E)

wherein
R$^2$ is C$_1$-C$_6$alkyl, C$_3$-C$_6$cycloalkyl, or aryl; and
R$^3$ is H, D, or a protecting group;
wherein the compound has a deuterium incorporation of at least 90% at the position specified as deuterium.

In certain embodiments, R$^2$ is isopropyl, t-butyl, isobutyl or phenyl.

In certain embodiments, R$^3$ is a protecting group selected from —C(O)H, —C(O)—X—C$_1$-C$_6$alkyl, —C(O)—X—C$_3$-C$_6$cycloalkyl, —C(O)—X—CH$_2$-aryl, —C(O)—X-aryl, —CH$_2$-aryl, —S(O$_2$)—C$_1$-C$_6$alkyl, or S(O$_2$)-aryl, wherein X is absent, O or NR$^5$, wherein R$^5$ is H or C$_1$-C$_6$alkyl. In certain embodiments, R$^3$ is a protecting group selected from —C(O)—X—C$_1$-C$_6$alkyl, —C(O)—X—C$_3$-C$_6$cycloalkyl, —C(O)—X-aryl, wherein X is absent, O, NH, or S. In certain embodiments, R$^3$ is t-butyloxycarbonyl (Boc), benzyl, benzyloxycarbonyl (Cbz), formyl or methoxycarbonyl (Moc).

In another aspect, the invention provides a method for preparing a compound represented by the structure (D):

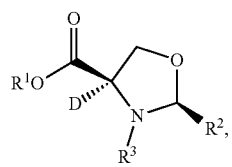
(D)

wherein
R$^1$ is H, C$_1$-C$_6$alkyl, C$_3$-C$_6$cycloalkyl, —CH$_2$-aryl, or aryl;
R$^2$ is C$_1$-C$_6$alkyl, C$_3$-C$_6$cycloalkyl, or aryl; and
R$^3$ is H, D, or a protecting group;
wherein the compound has a deuterium incorporation of at least 90% at the position specified as deuterium. The method comprises the steps of:
contacting a compound represented by the structure (B)

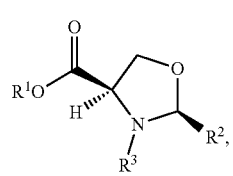
(B)

in which R$^1$, R$^2$, and R$^3$ are as defined for the compound of Formula (D);
with a base to form a reaction mixture; and
contacting the reaction mixture with at least 1 equivalent of a deuterium source;
under conditions such that the compound of structure (D) is formed;
wherein the compound of structure (D) has a deuterium incorporation of at least 90% at the position specified as deuterium. In certain embodiments, the base is selected from mesityllithium, 2,6-dimethoxyphenyllithium, 2,4,6-trimethoxyphenyllithium, tolyllithium, t-butyllithium, phenyllithium, lithium hexamethyldisilazide (LHMDS), trityllithium, phenylsodium and tritylsodium. In certain embodiments, the deuterium source is D$_2$O. In certain embodiments, the deuterium source is CH$_3$CO$_2$D (DOAc). In certain embodiments, the method comprises contacting the reaction mixture with 1-10 equivalents of the deuterium source.

In certain embodiments, the step of contacting the compound represented by structure "B" with the base to form the reaction mixture occurs at a temperature in the range from −100° C. to −50° C. In certain embodiments, the temperature is a temperature in the range from about −90° C. to about −60° C. In certain embodiments, the temperature is a temperature in the range from about −80° C. to about −60° C.

In certain embodiments, the step of contacting the compound represented by structure "B" with the base to form the reaction mixture occurs in an aprotic solvent. In specific embodiments, the aprotic solvent is THF, hexanes or heptane, or mixtures thereof.

In certain embodiments, the time during which the compound represented by structure "B" is contacted with the base to form the reaction mixture is a time in the range from 5 minutes to 2 hours. In certain embodiments, the time is a time in the range from 30 minutes to 2 hours. In certain specific embodiments, the time is about 30 minutes. In certain specific embodiments, the time is about 60 minutes.

In certain embodiments, the step of contacting the compound represented by structure "B" with the base to form the reaction mixture occurs under an inert atmosphere. In certain embodiments, the reaction mixture is contacted with less than 10 equivalents of the deuterium source (i.e., less than 10 moles of deuterium source per mole of Compound "B"). In more specific embodiments, the reaction mixture is contacted with less than 5 equivalents of the deuterium source. In certain specific embodiments, the reaction mixture is contacted with 3 to 4 equivalents of the deuterium source. In certain specific embodiments, the reaction mixture is contacted with 1 to 2 equivalents of the deuterium source. In certain specific embodiments, the reaction mixture is contacted with 3 equivalents of the deuterium source. In certain specific embodiments, the reaction mixture is contacted with 4 equivalents of the deuterium source.

In certain embodiments, the compound represented by the structure (D) is not isolated.

In another aspect, the invention provides a method for preparing a compound represented by the structure (E):

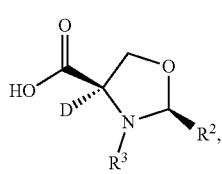

(E)

wherein
R² is C₁-C₆alkyl, C₃-C₆cycloalkyl, or aryl; and
R³ is H, D, or a protecting group;
wherein the compound has a deuterium incorporation of at least 90% at the position specified as deuterium. The method comprises the steps of:
(i) contacting a compound represented by structure (B)

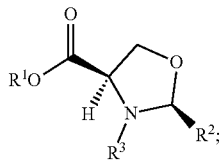

(B)

in which R¹, R², and R³ are as defined for the compound of Formula (E) with a base to form a reaction mixture;
(ii) contacting the reaction mixture with a deuterium source;
under conditions such that the compound represented by structure (D) is formed:

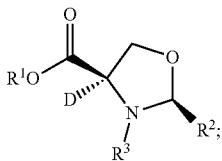

(D)

and
(iii) reacting the compound of structure (D) with a base to form the compound of structure (E);
wherein the compound of structure (E) has a deuterium incorporation of at least 90% at the position specified as deuterium. In certain embodiments, the base in step (i) is selected from mesityllithium, 2,6-dimethoxyphenyllithium, 2,4,6-trimethoxyphenyllithium, tolyllithium, t-butyllithium, phenyllithium, lithium hexamethyldisilazide (LHMDS), trityllithium, phenylsodium and tritylsodium. In certain embodiments, the deuterium source is D₂O. In certain embodiments, the deuterium source is CH₃CO₂D (DOAc). In certain embodiments, the method comprises contacting the reaction mixture with 1-10 equivalents of the deuterium source. In certain embodiments, the base in step (iii) is selected from LiOD, NaOD, KOD and Mg(OD)₂. In certain embodiments, the base in step (iii) is LiOD. In certain embodiments, the compound of structure (E) is formed without isolation of the compound of structure (D).

In another aspect, the invention provides a method for preparing a compound represented by the structure (D):

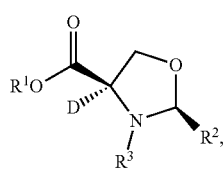

(D)

wherein
R¹ is H, C₁-C₆alkyl, C₃-C₆cycloalkyl, —CH₂-aryl, or aryl;
R² is C₁-C₆alkyl, C₃-C₆cycloalkyl, or aryl; and
R³ is H, D, or a protecting group;
wherein the compound has a deuterium incorporation of at least 90% at the position specified as deuterium. The method comprises the steps of:
contacting a compound represented by the structure (B')

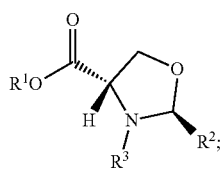

(B')

in which R¹, R², and R³ are as defined for the compound of Formula (D);
with a base to form a reaction mixture; and
contacting the reaction mixture with at least 1 equivalent of a deuterium source;
under conditions such that the compound of structure (D) is formed;
wherein the compound of structure (D) has a deuterium incorporation of at least 90% at the position specified as deuterium. In certain embodiments, the base is selected from mesityllithium, 2,6-dimethoxyphenyllithium, 2,4,6-trimethoxyphenyllithium, tolyllithium, t-butyllithium, phenyllithium, lithium hexamethyldisilazide (LHMDS), trityllithium, phenylsodium and tritylsodium. In certain embodiments, the deuterium source is D₂O. In certain embodiments, the deuterium source is CH₃CO₂D (DOAc). In certain embodiments, the method comprises contacting the reaction mixture with 1-10 equivalents of the deuterium source.

In certain embodiments, the step of contacting the compound represented by structure "B'" with the base to form the reaction mixture occurs at a temperature in the range from −100° C. to −50° C. In certain embodiments, the temperature is a temperature in the range from about −90° C. to about −60° C. In certain embodiments, the temperature is a temperature in the range from about −80° C. to about −60° C.

In certain embodiments, the step of contacting the compound represented by structure "B'" with the base to form the reaction mixture occurs in an aprotic solvent. In specific embodiments, the aprotic solvent is THF, hexanes or heptane, or mixtures thereof.

In certain embodiments, the time during which the compound represented by structure "B'" is contacted with the base to form the reaction mixture is a time in the range from 5 minutes to 2 hours. In certain embodiments, the time is a time in the range from 30 minutes to 2 hours. In certain specific embodiments, the time is about 30 minutes. In certain specific embodiments, the time is about 60 minutes.

In certain embodiments, the step of contacting the compound represented by structure "B'" with the base to form the reaction mixture occurs under an inert atmosphere.

In certain embodiments, the reaction mixture is contacted with less than 10 equivalents of the deuterium source (i.e., less than 10 moles of deuterium source per mole of Compound "B'"). In more specific embodiments, the reaction mixture is contacted with less than 5 equivalents of the deuterium source. In certain specific embodiments, the reaction mixture is contacted with 3 to 4 equivalents of the deuterium source. In certain specific embodiments, the reaction mixture is contacted with 1 to 2 equivalents of the deuterium source. In certain specific embodiments, the reaction mixture is contacted with 3 equivalents of the deuterium source. In certain specific embodiments, the reaction mixture is contacted with 4 equivalents of the deuterium source.

In another aspect, the invention provides a method for preparing a compound represented by the structure (E):

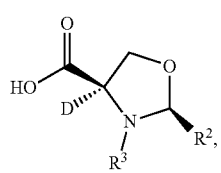

wherein
R² is C₁-C₆alkyl, C₃-C₆cycloalkyl, or aryl; and
R³ is H, D, or a protecting group;
wherein the compound has a deuterium incorporation of at least 90% at the position specified as deuterium. The method comprises the steps of:

(iv) contacting a compound represented by structure (B')

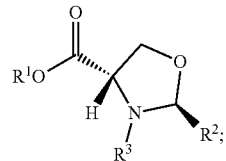

in which R¹, R², and R³ are as defined for the compound of Formula (E) with a base to form a reaction mixture;
(v) contacting the reaction mixture with a deuterium source;
under conditions such that the compound represented by structure (D) is formed:

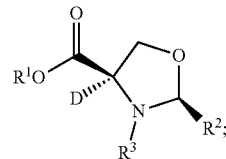

and
(vi) reacting the compound of structure (D) with a base to form the compound of structure (E);
wherein the compound of structure (E) has a deuterium incorporation of at least 90% at the position specified as deuterium. In certain embodiments, the base in step (i) is selected from mesityllithium, 2,6-dimethoxyphenyllithium, 2,4,6-trimethoxyphenyllithium, tolyllithium, t-butyllithium, phenyllithium, lithium hexamethyldisilazide (LHMDS), trityllithium, phenylsodium and tritylsodium. In certain embodiments, the deuterium source is D₂O. In certain embodiments, the deuterium source is CH₃CO₂D (DOAc). In certain embodiments, the method comprises contacting the reaction mixture with 1-10 equivalents of the deuterium source. In certain embodiments, the base in step (iii) is selected from LiOD, NaOD, KOD and Mg(OD)₂. In certain embodiments, the base in step (iii) is LiOD.

In another aspect, the invention provides a method for preparing a compound represented by the structure (D):

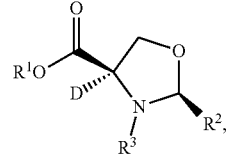

wherein
R¹ is H, C₁-C₆alkyl, C₃-C₆cycloalkyl, —CH₂-aryl, or aryl;
R² is C₁-C₆alkyl, C₃-C₆cycloalkyl, or aryl; and
R³ is H, D, or a protecting group;
wherein the compound has a deuterium incorporation of at least 90% at the position specified as deuterium. The method comprises the steps of:

contacting a compound represented by the structure (B‴)

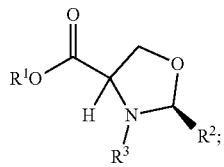

in which $R^1$, $R^2$, and $R^3$ are as defined for the compound of Formula (D);
with a base to form a reaction mixture; and
contacting the reaction mixture with at least 1 equivalent of a deuterium source;
under conditions such that the compound of structure (D) is formed;
wherein the compound of structure (D) has a deuterium incorporation of at least 90% at the position specified as deuterium. In certain embodiments, the base is selected from mesityllithium, 2,6-dimethoxyphenyllithium, 2,4,6-trimethoxyphenyllithium, tolyllithium, t-butyllithium, phenyllithium, lithium hexamethyldisilazide (LHMDS), trityllithium, phenylsodium and tritylsodium. In certain embodiments, the deuterium source is $D_2O$. In certain embodiments, the deuterium source is $CH_3CO_2D$ (DOAc). In certain embodiments, the method comprises contacting the reaction mixture with 1-10 equivalents of the deuterium source.

In certain embodiments, the step of contacting the compound represented by structure "B‴" with the base to form the reaction mixture occurs at a temperature in the range from −100° C. to −50° C. In certain embodiments, the temperature is a temperature in the range from about −90° C. to about −60° C. In certain embodiments, the temperature is a temperature in the range from about −80° C. to about −60° C.

In certain embodiments, the step of contacting the compound represented by structure "B‴" with the base to form the reaction mixture occurs in an aprotic solvent. In specific embodiments, the aprotic solvent is THF, hexanes or heptane, or mixtures thereof.

In certain embodiments, the time during which the compound represented by structure "B‴" is contacted with the base to form the reaction mixture is a time in the range from 5 minutes to 2 hours. In certain embodiments, the time is a time in the range from 30 minutes to 2 hours. In certain specific embodiments, the time is about 30 minutes. In certain specific embodiments, the time is about 60 minutes.

In certain embodiments, the step of contacting the compound represented by structure "B‴" with the base to form the reaction mixture occurs under an inert atmosphere.

In certain embodiments, the reaction mixture is contacted with less than 10 equivalents of the deuterium source (i.e., less than 10 moles of deuterium source per mole of Compound "B‴"). In more specific embodiments, the reaction mixture is contacted with less than 5 equivalents of the deuterium source. In certain specific embodiments, the reaction mixture is contacted with 3 to 4 equivalents of the deuterium source. In certain embodiments, the reaction mixture is contacted with 1 to 2 equivalents of the deuterium source. In certain specific embodiments, the reaction mixture is contacted with 3 equivalents of the deuterium source. In certain specific embodiments, the reaction mixture is contacted with 4 equivalents of the deuterium source.

In another aspect, the invention provides a method for preparing a compound represented by the structure (E):

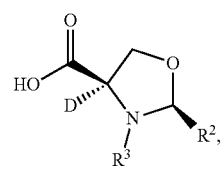

wherein
$R^2$ is $C_1$-$C_6$alkyl, $C_3$-$C_6$cycloalkyl, or aryl; and
$R^3$ is H, D, or a protecting group;
wherein the compound has a deuterium incorporation of at least 90% at the position specified as deuterium. The method comprises the steps of:
(vii) contacting a compound represented by structure (B‴)

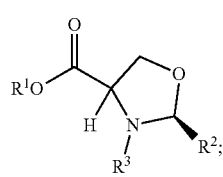

in which $R^1$, $R^2$, and $R^3$ are as defined for the compound of Formula (E) with a base to form a reaction mixture;
(viii) contacting the reaction mixture with a deuterium source;
under conditions such that the compound represented by structure (D) is formed:

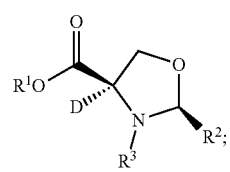

and
(ix) reacting the compound of structure (D) with a base to form the compound of structure (E);
wherein the compound of structure (E) has a deuterium incorporation of at least 90% at the position specified as deuterium. In certain embodiments, the base in step (i) is selected from mesityllithium, 2,6-dimethoxyphenyllithium, 2,4,6-trimethoxyphenyllithium, tolyllithium, t-butyllithium, phenyllithium, lithium hexamethyldisilazide (LHMDS), trityllithium, phenylsodium and tritylsodium. In certain embodiments, the deuterium source is $D_2O$. In certain embodiments, the deuterium source is $CH_3CO_2D$ (DOAc). In certain embodiments, the method comprises contacting the reaction mixture with 1-10 equivalents of the deuterium source. In certain embodiments, the base in step (iii) is selected from LiOD, NaOD, KOD and $Mg(OD)_2$. In certain embodiments, the base in step (iii) is LiOD.

In another aspect, the invention provides a method for preparing D-serine-2-d, the method comprising the steps of:
(i) contacting a compound of Formula B

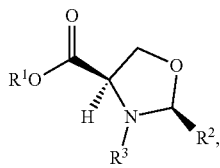

(B)

wherein
$R_1$ is H, $C_1$-$C_6$alkyl, $C_3$-$C_6$cycloalkyl, —$CH_2$-aryl, or aryl;
$R^2$ is $C_1$-$C_6$alkyl, $C_3$-$C_6$cycloalkyl, or aryl; and
$R^3$ is H, D, or a protecting group,
with a base to form a first reaction mixture;
(ii) contacting the first reaction mixture with a deuterium source to form a second reaction mixture;
(iii) contacting the second reaction mixture with a base to form a third reaction mixture;
and
(iv) contacting the third reaction mixture with acid under conditions such that D-serine-2-d is formed;
wherein the D-serine-2-d has a deuterium incorporation of at least 90% at the position specified as deuterium.

A method for preparing D-serine-2-d, the method comprising the steps of:
(i) contacting a compound of Formula B:

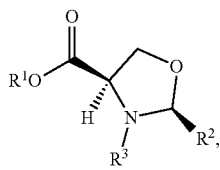

(B)

wherein
$R_1$ is H, $C_1$-$C_6$alkyl, $C_3$-$C_6$cycloalkyl, —$CH_2$-aryl, or aryl;
$R^2$ is $C_1$-$C_6$alkyl, $C_3$-$C_6$cycloalkyl, or aryl; and
$R^3$ is H, D, or a protecting group,
with a base to form a first reaction mixture;
(ii) contacting the first reaction mixture with a deuterium source to form a second reaction mixture;
(iii) contacting the second reaction mixture with a base to form a compound of Formula E;

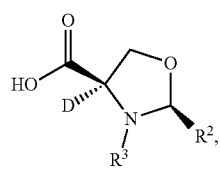

(E)

wherein
$R^2$ is $C_1$-$C_6$alkyl, $C_3$-$C_6$cycloalkyl, or aryl; and
$R^3$ is H, D, or a protecting group;
and
(iv) contacting the compound of formula E with acid under conditions such that D-serine-2-d is formed;
wherein the D-serine-2-d has a deuterium incorporation of at least 90% at the position specified as deuterium.

In certain embodiments, the method further comprises isolating Compound E prior to step (iv).

In another aspect, the invention provides compound (30b):

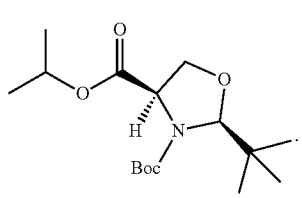

(30b)

In certain embodiments, compound (30b) has at least 90% stereometric purity.

In another aspect, the invention provides compound (30c):

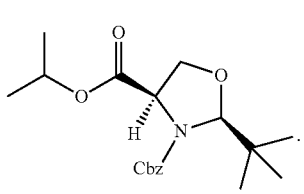

(30c)

In certain embodiments, compound (30c) has at least 90% stereometric purity.

In another aspect, the invention provides compound (30d):

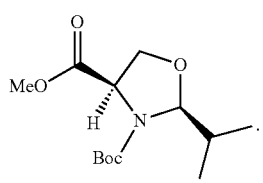

(30d)

In certain embodiments, compound (30d) has at least 90% stereometric purity.

In another aspect, the invention provides compound (30e):

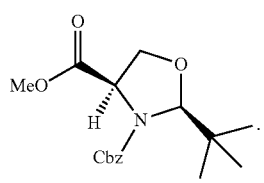

(30e)

In certain embodiments, compound (30e) has at least 90% stereometric purity.

In another aspect, the invention provides compound (40a):

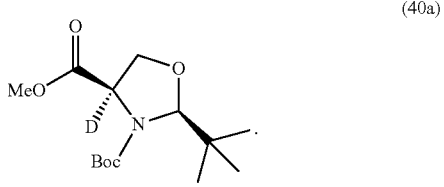 [SMILES: [2H][C@]1(C(=O)OC)CO[C@@H](C(C)(C)C)N1C(=O)OC(C)(C)C]

(40a)

In certain embodiments, compound (40a) has a deuterium incorporation of at least 90% at the position specified as deuterium. In certain embodiments, compound (40a) has at least 90% stereometric purity.

In another aspect, the invention provides compound (40b):

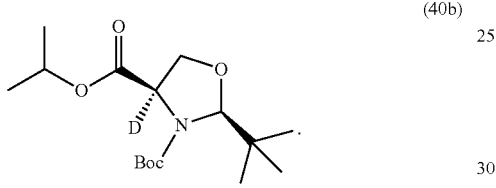

(40b)

In certain embodiments, compound (40b) has a deuterium incorporation of at least 90% at the position specified as deuterium. In certain embodiments, compound (40b) has at least 90% stereometric purity.

In another aspect, the invention provides compound (40c):

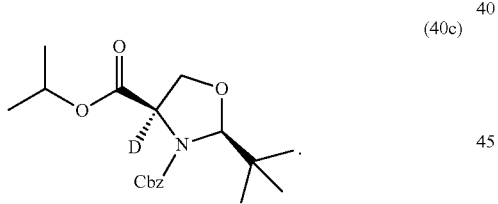

(40c)

In certain embodiments, compound (40c) has a deuterium incorporation of at least 90% at the position specified as deuterium. In certain embodiments, compound (40c) has at least 90% stereometric purity.

In another aspect, the invention provides compound (40d):

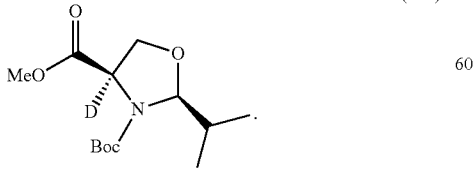

(40d)

In certain embodiments, compound (40d) has a deuterium incorporation of at least 90% at the position specified as deuterium. In certain embodiments, compound (40d) has at least 90% stereometric purity.

In another aspect, the invention provides compound (40e):

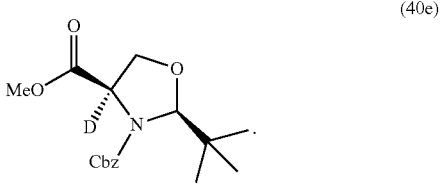 [SMILES: [2H][C@]1(C(=O)OC)CO[C@@H](C(C)(C)C)N1C(=O)OCc1ccccc1]

(40e)

In certain embodiments, compound (40e) has a deuterium incorporation of at least 90% at the position specified as deuterium. In certain embodiments, compound (40e) has at least 90% stereometric purity.

In another aspect, the invention provides compound (50):

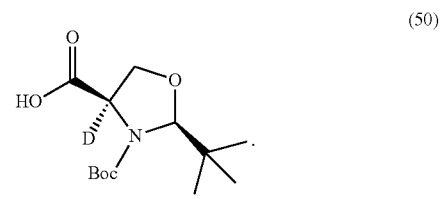 [SMILES: [2H][C@]1(C(=O)O)CO[C@@H](C(C)(C)C)N1C(=O)OC(C)(C)C]

(50)

In certain embodiments, compound (50) has a deuterium incorporation of at least 90% at the position specified as deuterium. In certain embodiments, compound (50) has at least 90% stereometric purity.

In another aspect, the invention provides compound (50c):

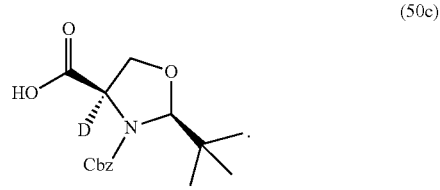 [SMILES: [2H][C@]1(C(=O)O)CO[C@@H](C(C)(C)C)N1C(=O)OCc1ccccc1]

(50c)

In certain embodiments, compound (50c) has a deuterium incorporation of at least 90% at the position specified as deuterium. In certain embodiments, compound (50c) has at least 90% stereometric purity.

In another aspect, the invention provides compound (50d):

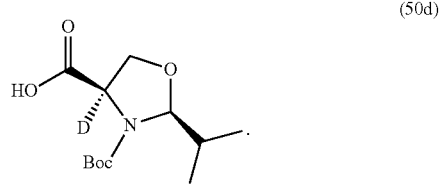 [SMILES: [2H][C@]1(C(=O)O)CO[C@@H](C(C)C)N1C(=O)OC(C)(C)C]

(50d)

In certain embodiments, compound (50d) has a deuterium incorporation of at least 90% at the position specified as deuterium. In certain embodiments, compound (50d) has at least 90% stereometric purity.

In another aspect, the invention provides a method for preparing compound 40a:

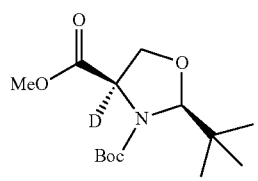

(40a)

the method comprising the steps of:
contacting compound 30a'

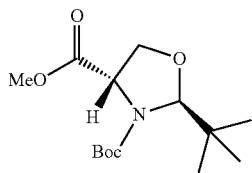

(30a')

with a base to form a reaction mixture; and
contacting the reaction mixture with 1-10 equivalents of a deuterium source;
under conditions such that compound 40a is formed;
wherein the compound 40a has a deuterium incorporation of at least 90% at the position specified as deuterium.

In certain embodiments, compound 40a is not isolated.

In another aspect, the invention provides a method for preparing compound 40a:

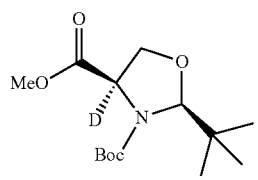

(40a)

the method comprising the steps of:
contacting compound 30a"

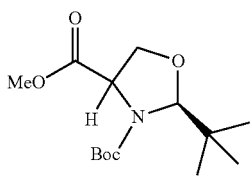

(30a")

with a base to form a reaction mixture; and
contacting the reaction mixture with 1-10 equivalents of a deuterium source;
under conditions such that compound 40a is formed;
wherein the compound 40a has a deuterium incorporation of at least 90% at the position specified as deuterium.

In certain embodiments, compound 40a is not isolated.

In another aspect, the invention provides a method for preparing compound 40b:

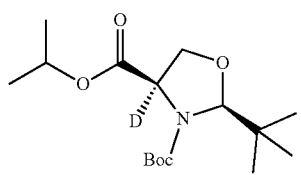

(40b)

the method comprising the steps of:
contacting compound 30b'

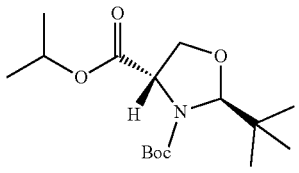

(30b')

with a base to form a reaction mixture; and
contacting the reaction mixture with 1-10 equivalents of a deuterium source;
under conditions such that compound 40b is formed;
wherein the compound 40b has a deuterium incorporation of at least 90% at the position specified as deuterium.

In certain embodiments, compound 40b is not isolated.

In another aspect, the invention provides a method for preparing compound 40b:

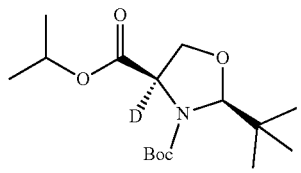

(40b)

the method comprising the steps of:
contacting compound 30b"

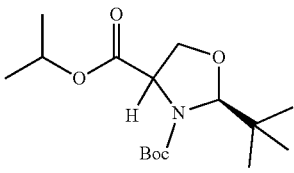

(30b")

with a base to form a reaction mixture; and
contacting the reaction mixture with 1-10 equivalents of a deuterium source;
under conditions such that compound 40b is formed;
wherein the compound 40b has a deuterium incorporation of at least 90% at the position specified as deuterium.

In certain embodiments, compound 40b is not isolated.

In another aspect, the invention provides a method for preparing D-serine-2-d, the method comprising:
contacting compound 50:

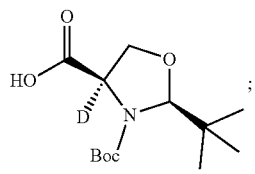

(50)

with acid under conditions such that D-serine-2-d is formed; wherein the D-serine-2-d has a deuterium incorporation of at least 90% at the position specified as deuterium.

In certain embodiments, the acid is HCl.

In another aspect, the invention provides a method for preparing D-serine-2-d, the method comprising the steps of:
(i) contacting compound 30a

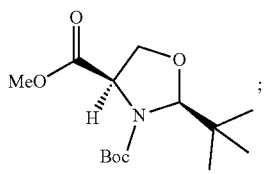

(30a)

with a base to form a reaction mixture; and
(ii) contacting the reaction mixture with 1-10 equivalents of a deuterium source;
under conditions such that compound 40a is formed

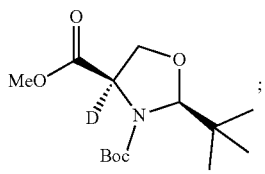

(40a)

(iii) contacting compound 40a with a base under conditions such that compound 50 is formed

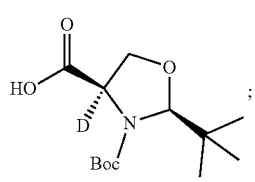

(50)

and
(iv) contacting compound 50 with acid under conditions such that D-serine-2-d is formed;
wherein the D-serine-2-d has a deuterium incorporation of at least 90% at the position specified as deuterium.

In certain embodiments, the base in step (i) is mesityllithium. In certain embodiments, the base in step (i) is 2,6-dimethoxyphenyllithium. In certain embodiments, the base in step (i) is 2,4,6-trimethoxyphenyllithium. In certain embodiments, the base in step (iii) is lithium deuteroxide. In certain embodiments, the acid in step (iv) is HCl. In certain embodiments, compound 40a is not isolated.

In another aspect, the invention provides a method for preparing D-serine-2-d, the method comprising the steps of:
a) contacting compound 30b

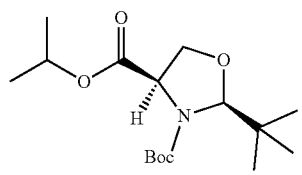

(30b)

with a base to form a reaction mixture; and
b) contacting the reaction mixture with 1-10 equivalents of a deuterium source;
under conditions such that compound 40b is formed

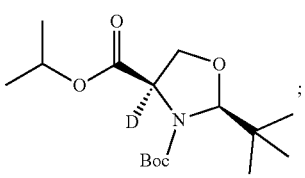

(40b)

c) contacting compound 40b with a base under conditions such that compound 50 is formed

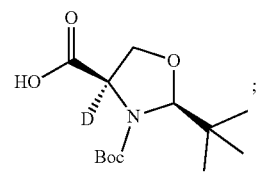

(50)

and
d) contacting compound 50 with acid under conditions such that D-serine-2-d is formed;
wherein the D-serine-2-d has a deuterium incorporation of at least 90% at the position specified as deuterium.

In certain embodiments, the base in step (a) is tolyllithium. In certain embodiments, the base in step (a) is 2,6-dimethoxyphenyllithium. In certain embodiments, the base in step (a) is 2,4,6-trimethoxyphenyllithium. In certain embodiments, the base in step (c) is lithium deuteroxide. In certain embodiments, the acid in step (d) is HCl. In certain embodiments, compound 40b is not isolated.

In another aspect, the invention provides method for preparing compound 50,

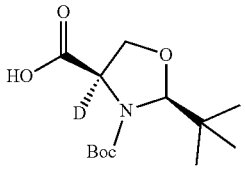
(50)

the method comprising the steps of:

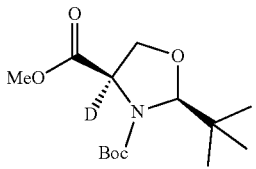
(40a)

reacting compound 40a with 1-10 equivalents of lithium deuteroxide to form compound 50.

In certain embodiments, the compound 50 has a deuterium incorporation of at least 90% at the position specified as deuterium.

In certain embodiments, compound 40a is not isolated.

In another aspect, the invention provides method for preparing compound 50,

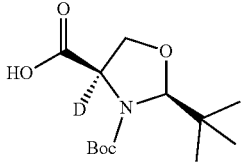
(50)

the method comprising the steps of:

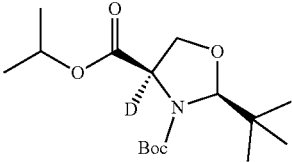
(40b)

reacting compound 40b with 1-10 equivalents of lithium deuteroxide to form compound 50.

In certain embodiments, the compound 50 has a deuterium incorporation of at least 90% at the position specified as deuterium.

In certain embodiments, compound 40b is not isolated.

Definitions

The term "alkyl" refers to a monovalent saturated hydrocarbon group. A $C_1$-$C_4$ alkyl is an alkyl having from 1 to 4 carbon atoms; a $C_1$-$C_6$ alkyl is an alkyl having from 1 to 6 carbon atoms. In some embodiments, an alkyl may be linear or branched. In some embodiments, an alkyl may be primary, secondary, or tertiary. Non-limiting examples of alkyl groups include methyl; ethyl; propyl, including n-propyl and isopropyl; butyl, including n-butyl, isobutyl, sec-butyl, and t-butyl; pentyl, including, for example, n-pentyl, isopentyl, and neopentyl; and hexyl, including, for example, n-hexyl and 2-methylpentyl. Non-limiting examples of primary alkyl groups include methyl, ethyl, n-propyl, n-butyl, n-pentyl, and n-hexyl. Non-limiting examples of secondary alkyl groups include isopropyl, sec-butyl, and 2-methylpentyl. Non-limiting examples of tertiary alkyl groups include t-butyl.

The term "cycloalkyl" refers to a monocyclic or bicyclic monovalent saturated hydrocarbon ring system. The term "$C_3$-$C_6$ cycloalkyl" refers to a cycloalkyl wherein the number of ring carbon atoms is from 3 to 10. Examples of $C_3$-$C_{10}$ cycloalkyl include $C_3$-$C_6$ cycloalkyl. Bicyclic ring systems include fused, bridged, and spirocyclic ring systems. More particular examples of cycloalkyl groups include, cyclopropyl, cyclobutyl, cyclopentyl, and cyclohexyl.

"Aryl" by itself or as part of another substituent refers to a monocyclic or polycyclic monovalent aromatic hydrocarbon group having the stated number of carbon atoms (i.e., $C_5$-$C_{14}$ means from 5 to 14 carbon atoms). Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octophene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthylene, and the like. In a specific embodiment, the aryl group is phenyl or naphthyl. In a more specific embodiment, the aryl group is phenyl.

An alkyl, cycloalkyl, or aryl group can optionally be substituted with one or more substituents such as halogen atoms (e.g., F, Cl, Br, or I). For example, a methyl group can be substituted with 1-3 halogen atoms. In certain embodiments, an alkyl, cycloalkyl, or aryl group is substituted with 0-6 halogen atoms.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Thus, for example, a nitrogen atom can be protected as a carbamate, e.g., with a protecting group such as t-butoxycarbonyl (Boc); as a sulfonamide, e.g., with a protecting group such as triflyl (Tf, $SO_2$—$CF_3$); as an amide, e.g., with a protecting group such as acetyl, benzoyl, or trifluoroacetyl ($F_3$—Ac); or as an amine, e.g., with a protecting group such as benzyl or trityl (Tr, —$CPh_3$. Adjustments to the protecting groups and formation and cleavage methods described herein may be adjusted as necessary in light of the various substituents.

It will be recognized that some variation of natural isotopic abundance occurs in a synthesized compound depending upon the origin of chemical materials used in the synthesis. Thus, a preparation of a deuterated compound will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention.

See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. However, in certain embodiments, where specifically stated, when a position is designated specifically as "H" or "hydrogen", the position has at least 80%, at least 90%, at least 95%, at least 96%, at least 97%, at least 98%, or at least 99% hydrogen. In some embodiments, where specifically stated, when a position is designated specifically as "H" or "hydrogen", the position incorporates ≤20% deuterium, ≤10% deuterium, ≤5% deuterium, ≤4% deuterium, ≤3% deuterium, ≤2% deuterium, or ≤1% deuterium. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In some embodiments, in a compound of this invention, each designated deuterium atom has deuterium incorporation of at least 52.5%. In some embodiments, in a compound of this invention, each designated deuterium atom has deuterium incorporation of at least 60%. In some embodiments, in a compound of this invention, each designated deuterium atom has deuterium incorporation of at least 67.5%. In some embodiments, in a compound of this invention, each designated deuterium atom has deuterium incorporation of at least 75%. In some embodiments, in a compound of this invention, each designated deuterium atom has deuterium incorporation of at least 80%. In some embodiments, in a compound of this invention, each designated deuterium atom has deuterium incorporation of at least 82.5%. In some embodiments, in a compound of this invention, each designated deuterium atom has deuterium incorporation of at least 85%. In some embodiments, in a compound of this invention, each designated deuterium atom has deuterium incorporation of at least 90%. In some embodiments, in a compound of this invention, each designated deuterium atom has deuterium incorporation of at least 95%. In some embodiments, in a compound of this invention, each designated deuterium atom has deuterium incorporation of at least 97.5%. In some embodiments, in a compound of this invention, each designated deuterium atom has deuterium incorporation of at least 99%. In some embodiments, in a compound of this invention, each designated deuterium atom has deuterium incorporation of at least 99.5%.

Deuterium incorporation in a compound of the invention can be measured using a variety of techniques, some of which are known in the art. For example, $^1$H NMR can be used to measure deuterium incorporation (e.g., by measuring the absence of or decrease in proton signals corresponding to deuterated positions, e.g., relative to a non-deuterated position or positions).

The term "isotopologue" refers to a molecule in which the chemical structure differs from another molecule of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure will contain molecules having deuterium at each of the positions designated as deuterium in the chemical structure, and may also contain isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. In certain embodiments, the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

D-Serine and deuterated analogs of D-serine (such as D-serine-2-d) contain an asymmetric carbon atom (i.e., the carbon bearing the —NH$_2$ group) and may contain one or more additional asymmetric carbon atoms. In certain embodiments, a deuterated D-serine analog (such as D-serine-2-d) is substantially free from other possible stereoisomers (such as a corresponding L-serine analog, such as L-serine-2-d). The term "substantially free of other stereoisomers" as used herein means less than 25% of other stereoisomers, preferably less than 10% of other stereoisomers, more preferably less than 5% of other stereoisomers, more preferably less than 2% of other stereoisomers, and still more preferably less than 1% of other stereoisomers, are present. In certain embodiments, a compound of the invention, or an intermediate used in the methods of the invention, has an enantiomeric excess (e.e.) of at least 95%, at least 96%, at least 97%, at least 98%, at least 99%, or at least 99.5%. The term "stereometric purity" as used herein refers to the level of purity of the particular stereoisomer specified relative to other possible stereoisomers (i.e. at least 90% stereometric purity for a compound containing one or more asymmetric carbon atoms means that 10% or less of other stereoisomers are present). Methods of obtaining or synthesizing an individual stereoisomer (e.g., enantiomer or diastereomer) for a given compound are known in the art and may be applied as practicable to final compounds or to starting material or intermediates.

Unless otherwise indicated, when a disclosed compound is named or depicted by a structure having one or more chiral centers of unspecified stereochemistry, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"Stereoisomer" refers to both enantiomers and diastereomers. "Tert" and "t-" each refer to tertiary. "Sec" or "s-" each refer to secondary. "n-" refers to normal. "i-" refers to iso.

"Substituted with deuterium" refers to the replacement of one or more hydrogen atoms with a corresponding number of deuterium atoms.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

In some embodiments, the compounds of the invention, or intermediates used in the preparation of compounds of the invention, are isolated or purified. The terms "isolated" and "purified", as used herein, mean that the compound or intermediate is at least partially or substantially separated from the environment in which it was formed or detected. For example, an "isolated" or "purified" compound or intermediate can be at least about 50%, at least about 60%, at least about 70%, at least about 80%, at least about 90%, at least about 95%, at least about 97%, or at least about 99% by weight of the compound or intermediate. Methods for isolating and purifying compounds and intermediates are known in the art, and include methods such as crystallization and chromatography.

Methods and Compounds for Preparing Deuterated Analogs of D-Serine

A general scheme for the preparation of D-serine-2-d is shown in the FIGURE.

As shown in the FIGURE, D-serine ester A is converted to the cis-diastereomer oxazolidine B by treatment with an aldehyde ($R^2C(O)H$)) such as pivalaldehyde or isobutyraldehyde, followed by protection of the amino group with a suitable protecting group $R^3$ (e.g., with an anhydride $R^3{}_2O$, such as BOC anhydride, a chloroformate $R^3Cl$, such as Cbz chloride, or a halide $R^3X$ such as benzyl bromide). Alternatively, L-serine ester A' is converted to the trans-diastereomer oxazolidine B' by protection of the amino group with a suitable protecting group $R^3$ (e.g., with an anhydride $R^3{}_2O$, such as BOC anhydride, a chloroformate $R^3Cl$, such as Cbz chloride, or a halide $R^3X$ such as benzyl bromide) followed by treatment with an aldehyde ($R^2C(O)H$)) such as pivalaldehyde or isobutyraldehyde.

Deprotonation of B or B' with a base results in formation of enolate C. While a variety of bases, including sterically-hindered bases, can be used (e.g., trityllithium, lithium diisopropyl amide (LDA), triisopropylphenyllithium, lithiumhexamethyldisilazide (LHMDS)), the use of mesityllithium has been found to produce high deuterium incorporation in the final product (see Example 1). Typical bases used for this type of reaction (LDA and LHMDS) produce conjugate acids with exchangeable hydrogen atoms and, as such, result in lower levels of % D observed for compound D. Phenyl lithium produced some of the desired product, but also resulted in some formation of a ketone byproduct. The use of either 2,6-dimethoxyphenyllithium or 2,4,6-trimethoxyphenyllithium provided multiple advantages: preparation was carried out at standard temperatures (0-20° C.) via direct ortholithiation from the 1,3-dimethoxybenzene or 1,3,5-trimethoxybenzene precursors; each base demonstrated stability at 0-20° C.; bromobutane was not generated as a byproduct; improved stability of the base allowed versatility in handling during addition to a solution of compound B; precursors 1,3-dimethoxybenzene and 1,3,5-trimethoxybenzene are commercially available and relatively inexpensive. In certain embodiments, the deprotonation reaction is performed at a temperature at or below −50 C, e.g., at or below −60° C., or at or below −75° C.

Enolate C is then contacted with a deuterium source $DOR^4$ (e.g., $D_2O$, methanol-d or methanol-$d_4$, acetic acid-d, or the like) to form the monodeuterated cis-diastereomer oxazolidine D. A deuterium source can be any suitable source of deuterons (i.e., the deuterium analog of a proton source). In certain embodiments, 1-10 equivalents or 1-5 equivalents (based on the amount of B) of deuterium source $DOR^4$ (e.g., $D_2O$) are used. In certain embodiments, 1-10 equivalents or 1-5 equivalents of $D_2O$ are used. A deuterium source can be any suitable source of deuterons (i.e., the deuterium analog of a proton source). In certain embodiments, the deuterium source is monobasic (i.e., each molecule of the deuterium source is capable of providing one deuteron). Non-limiting examples of monobasic deuterium sources include $D_2O$, $CH_3OD$, $CD_3OD$, DOAc, and the like. In certain embodiments, the deuterium source is polybasic (i.e., each molecule of the deuterium source is capable of providing two or more (e.g., 2 or 3) deuterons). Non-limiting examples of polybasic deuterium source include $D_2SO_4$, $D_3PO_4$, and the like. For the avoidance of doubt, an equivalent of a deuterium source, as used herein, refers to an amount of the deuterium source that is capable of providing a molar equivalent of deuteron. For example, 1-10 equivalent of a deuterium source can mean 1-10 equivalent of a monobasic source (e.g., $D_2O$, DOAc) or 0.5-5 equivalent of a dibasic source (e.g., $D_2SO_4$), etc.

Deprotection of cis-oxazolidine D to form D-serine-2-d (G) proceeds by removal of the ester group $R^1$ and the amine-protecting group $R^3$, and opening the oxazolidine ring. This can be accomplished, e.g., by ester hydrolysis (e.g., under basic conditions) to form acid E followed by removal of the amine-protecting group and opening the oxazolidine ring, or by opening the oxazolidine ring and removal of the amine-protecting group (e.g., removal of a BOC protecting group under acidic conditions) to form esterified deuterated D-serine F, followed by ester hydrolysis. Advantageously, it has been found that ester hydrolysis of cis-oxazolidine D to form acid E can occur without isolation of cis-oxazolidine D, e.g., by using $D_2O$ as the deuterium source for the deuteration step. Without being bound by any particular theory, it is believed that lithium deuteroxide resulting from the $D_2O$ quenching of the enolate C hydrolyzes the ester in situ without loss of deuterium at the specified position of cis-oxazolidine D. The transformation from oxazolidine B to acid E can thus be effected in one pot, without isolation of intermediates C or D.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include, by way of example and without limitation, halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof.

Suitable ether solvents include, by way of example and without limitation: dimethoxymethane, tetrahydrofuran, 2-methyltetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, mixtures thereof.

Suitable protic solvents can include, by way of example and without limitation, water (including $D_2O$), methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, and mixtures thereof.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide (DMSO), propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, hexamethylphosphoramide, and mixtures thereof.

Suitable hydrocarbon solvents include, by way of example and without limitation, benzene, cyclohexane, pentane, 2-methylpentane, hexane, toluene, cycloheptane, methylcyclohexane, heptane, ethylbenzene, m-, o-, or p-xylene, octane, indane, nonane, naphthalene, and mixtures thereof.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The reactions of the processes described herein can be carried out in air or under an inert atmosphere. Typically, reactions containing reagents or products that are substantially reactive with air can be carried out using air-sensitive synthetic techniques that are well known to the skilled artisan.

Examples of acids can be inorganic or organic acids. Non-limiting examples of inorganic acids include hydrochloric acid (HCl), hydrobromic acid, sulfuric acid, phosphoric acid, and nitric acid. Non-limiting examples of organic acids include formic acid, acetic acid, propionic acid, butanoic acid, benzoic acid, 4-nitrobenzoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

EXAMPLES

Example 1: Preparation of D-Serine-2-d (Compound 60)

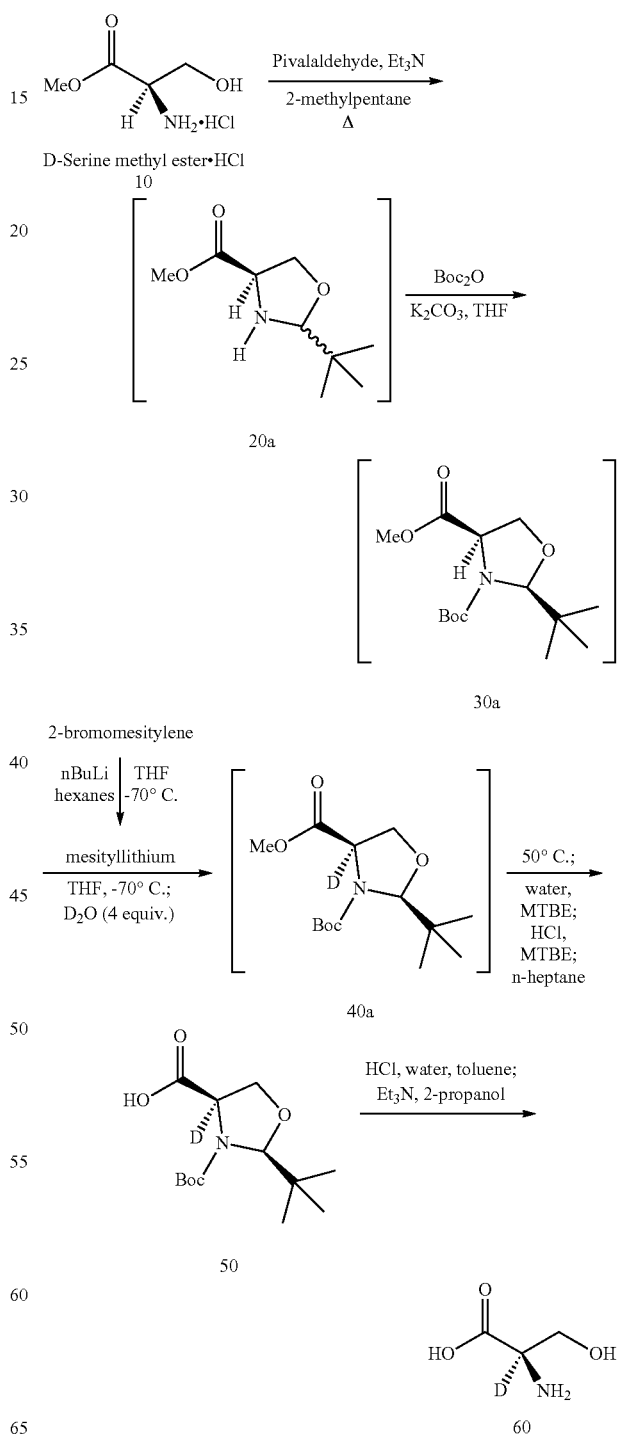

A process for preparing D-serine-2-d (60) began with a two-stage protection of D-serine methyl ester 10 (commercially available) to provide a solution of compound 30a as a single diastereomer. The preparation of 27 kg of the opposite diastereomer of compound 30a has been previously reported (Anson, M. S. et. al, Org. Process Res. Dev., 2011, 15, 389-397, the contents of which are incorporated herein by reference) using pivalaldehyde and isohexane (2-methylpentane) in a Dean-Stark distillation set-up. After t-butoxycarbonyl (BOC) protection of intermediate 20a using BOC anhydride, a solution of compound 30a was then charged to a cold solution of preformed mesityllithium in THF generating the lithium enolate of compound 30a, which was held below −60° C.

Subsequent quenching of the enolate with $D_2O$ (3-4 equiv) and warming to room temperature afforded compound 40a (>98% D) as a solution in THF. Ester hydrolysis to provide compound 50 was then achieved by warming the reaction mixture (which contained lithium deuteroxide) to 50° C. Cooling and subsequent dilution with water and methyl t-butyl ether (MTBE) resulted in a biphasic mixture with the lithium carboxylate of compound 50 retained in the aqueous phase and all organic impurities (mesitylene, 2-bromomesitylene, and the like) removed to the organic layer. Acidification of the aqueous layer and subsequent extraction with MTBE followed by crystallization from n-heptane provided carboxylic acid 50 as an isolated white crystalline solid (>98% D) which filtered well. Finally, treatment of compound 50 with hydrochloric acid provided compound 60 (D-serine-2-d) which was isolated as a crystalline solid upon pH adjustment and subsequent precipitation with 2-propanol. This crystalline material was found to be very clean except for some residual trimethylamine hydrochloride salt. Recrystallization of the crude 60 from 2-propanol/water provided the desired product.

Compound 30a:

Compound 30a was prepared from D-serine methyl ester hydrochloride following the procedure of Anson et al. noted above.

Compound 50:

2-Bromomesitylene (5.4 mL, 35.6 mmol, 1.2 equiv) was added to THF (60 mL) and the resulting solution was cooled to −75° C. A 2.5 M solution of n-butyllithium in hexanes (13.0 mL, 32.6 mmol, 1.1 equiv) was then added dropwise at such a rate to maintain the reaction temperature below −60° C. After stirring at −75° C. for 30 minutes, a solution of Compound 30a (8.5 g, 29.7 mmol, 1.0 equiv) in THF (15 mL) was added dropwise at such a rate to maintain the reaction temperature below −60° C. After stirring at −75° C. for 30 minutes, $D_2O$ (2.2 mL, 119 mmol, 4.0 equiv) was added dropwise at such a rate to maintain the reaction temperature below −60° C. Once the addition was complete, the reaction was warmed to 50° C. and stirred at this temperature for 20 hours then cooled to 20° C. Water (75 mL) and MTBE (50 mL) were added and the biphasic mixture was stirred at 20° C. for 10 minutes. The upper layer (organic) was removed and the remaining aqueous solution was washed once with MTBE (50 mL).

The aqueous layer was then adjusted from pH ~13 to pH 2.5 with 1N HCl (27.4 mL) then extracted with MTBE (2×50 mL). The MTBE extracts were combined, dried with $MgSO_4$, filtered and concentrated to dryness to afford Compound 50 as a clear oil that crystallized upon standing. Compound 50 was then recrystallized from n-heptane (30 mL) by heating the suspension to reflux until complete dissolution was observed then slowly cooling to 10° C. After stirring at 10° C. for 20 minutes, the mixture was filtered affording Compound 50 (6.1 g, 75% yield, 99% D) as a white crystalline solid. 400 MHz 1H NMR ($d_6$-DMSO, ppm) δ 12.83 (br s, 1H), 4.92 (s, 1H), 4.14 (d, J=8 Hz, 1H), 4.07 (d, J=8 Hz, 1H), 1.41 (s, 9H), 0.88 (s, 9H).

Compound 60 (D-Serine-2-d):

A mixture of Compound 50 (2.0 g, 7.30 mmol, 1.0 equiv), toluene (10 mL) and aqueous 6N HCl (4.25 mL, 25.5 mmol, 3.5 equiv) was stirred at 60° C. for 2 hours then cooled to 20° C. providing a biphasic mixture. The upper toluene layer was removed and the remaining aqueous phase was washed once with toluene (5 mL) then adjusted to pH 5 with triethylamine (~2.5 mL). 2-Propanol (20 mL) was then added slowly over 10 minutes and the resulting slurry was cooled to 10° C. After stirring at 10° C. for 20 minutes, the mixture was filtered and rinsed with 2-propanol (10 mL) affording Compound 60 (626 mg, 81% yield, 99% D) as a white crystalline solid. 400 MHz 1H NMR (0.7M NaOD/$D_2O$, ppm) δ 3.68 (d, J=12 Hz, 1H), 3.59 (d, J=12 Hz, 1H).

Example 2: Alternative Method of Preparing D-Serine-2-d (Compound 60)

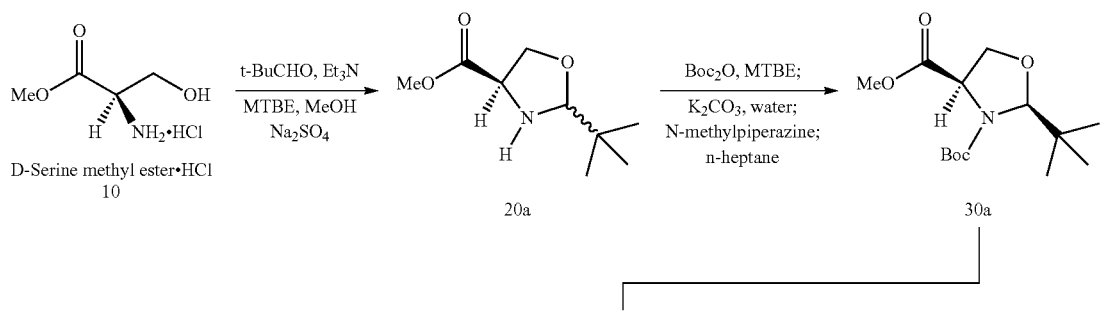

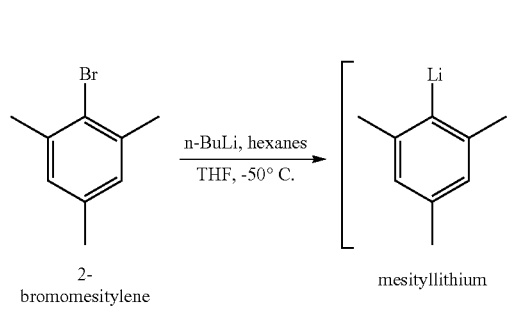
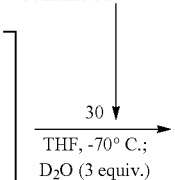
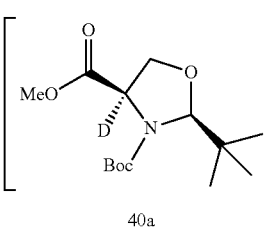
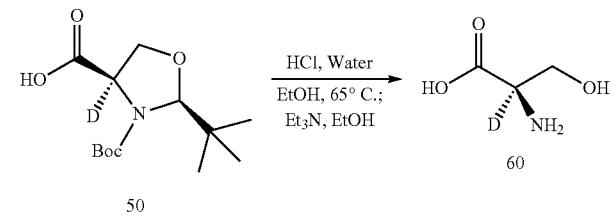

An alternate process for preparing D-serine-2-d began again with a two-stage protection of D-serine methyl ester 10 (commercially available) to provide compound 30a as a single diastereomer. A solution of compound 30a was then charged to a cold solution of preformed mesityllithium in THF generating the lithium enolate of compound 30a, which was held below −65° C.

Subsequent quenching of the enolate with D$_2$O (3 equiv) and warming to room temperature afforded compound 40a (>98% D) as a solution in THF. Ester hydrolysis to provide compound 50 was then achieved by warming the reaction mixture (which contained lithium deuteroxide) to 50° C. Cooling and subsequent dilution with water and methyl t-butyl ether (MTBE) resulted in a biphasic mixture with the lithium carboxylate of compound 50 retained in the aqueous phase and all organic impurities (mesitylene, 2-bromomesitylene, and the like) removed to the organic layer. Acidification of the aqueous layer and subsequent extraction with MTBE followed by crystallization from n-heptane provided carboxylic acid 50 as an isolated white crystalline solid (>98% D) which filters well. Finally, treatment of compound 50 with hydrochloric acid provided compound 60 (D-serine-2-d) which was isolated as a crystalline solid upon pH adjustment and subsequent precipitation with ethanol. This crystalline material was found to be very clean except for some residual triethylamine hydrochloride salt. Recrystallization of the crude 60 from ethanol/water provided the desired product. During the recrystallization step, the aqueous solution of compound 60 was filtered to remove insoluble impurities prior to the addition of ethanol.

Compound 30a:

D-Serine methyl ester hydrochloride 10 (100 g, 643 mmol, 1.0 equiv) was added to a suspension of sodium sulfate (183 g, 1290 mmol, 2.0 equiv) in tert-butyl methyl ether (400 mL). Methanol (50 mL) was then added followed by pivalaldehyde (77 mL, 690 mmol, 1.1 equiv) and triethylamine (90 mL, 643 mmol, 1.0 equiv). After stirring at 20-25° C. for 3 hours, n-heptane (500 mL) was added then the batch was stirred for an additional 15 minutes. The resulting suspension was then filtered, and the reactor and filter cake were washed with additional n-heptane (600 mL). To the combined filtrate was added a solution of di-tert-butyl dicarbonate (140 g, 643 mmol, 1.0 equiv) in n-heptane (50 mL). After stirring at 20-25° C. for 12 hours, a solution of potassium carbonate (300 mL of a 20% w/w solution in water) was added. After stirring at 20-25° C. for 12 hours, the aqueous phase was removed and N-methylpiperazine (25 mL, 225 mmol, 0.35 equiv) was added to the organic layer. After stirring at 20-25° C. for 1 hour the reaction was washed successively with 0.5 N HCl (600 mL), 20% potassium carbonate (400 mL) and water (300 mL). The batch was then concentrated by vacuum to a clear oil. n-Heptane (500 mL) was then added and the batch was washed three times with water (3×300 mL). The resulting solution was then concentrated by vacuum to a neat oil. n-Heptane (300 mL) was then added and the batch was again concentrated to provide compound 30a as a neat oil. 1H NMR (400 MHz, DMSO-d$_6$) δ 4.91 (s, 1H), 4.71 (t, J=6.8 Hz, 1H), 4.12 (d, J=6.8 Hz, 1H), 3.67 (s, 3H), 1.40 (s, 9H), 0.86 (s, 9H).

Compound 50:

2-Bromomesitylene (639 mL, 4.3 mol, 1.2 equiv) was added to THF (6.0 L) and the resulting solution was cooled to −65° C. A 2.5 M solution of n-butyllithium in hexanes (1.5 L, 3.8 mol, 1.1 equiv) was then added at such a rate to maintain the reaction temperature below −50° C. After stirring at −50° C. for 60 minutes, the resulting white suspension was cooled to −75° C. and a solution of Compound 30a (1000 g, 3.5 mol, 1.0 equiv) in heptane (960 mL) was added at such a rate to maintain the reaction temperature below −65° C. (THF was also used successfully in place of heptane). After stirring at −75° C. for 60 minutes, a solution of D$_2$O (188.4 mL, 10.4 mol, 3.0 equiv) in THF (750 mL) was added at such a rate to maintain the reaction temperature below −65° C. Once the addition was complete, the reaction was warmed to 50° C. and stirred at this temperature for 15 hours then cooled to 20° C. Water (4.0 L) and MTBE (3.0 L) were added and the biphasic mixture was stirred at 20° C. for 15 minutes. The bottom layer (aqueous) was retained and the upper layer (organic) was extracted with water (1.0 L). The aqueous phases were combined and washed once with MTBE (2.0 L). MTBE (4.0 L) was then added to the aqueous solution and the mixture was acidified to pH 3.0 with 3.0 N HCl (1.3 L). The phases were then split and the aqueous phase was extracted with MTBE (1.0 L). The organic phases were combined, washed with water (1.0 L) then concentrated by vacuum to a total volume of 2.0 L. n-Heptane (6.0 L) was then charged and the resulting mixture was concentrated by vacuum at 75° C. to a total volume of 5.0 L. The resulting white suspension was stirred at 85° C. until complete dissolution was achieved then was cooled to 20° C. and filtered. The filter cake was washed with cold n-heptane (500 mL) and dried by vacuum at 60° C. to afford Compound 50 (788 g, 82% yield, >99% D) as a white crystalline solid. 400 MHz 1H NMR (d$_6$-DMSO, ppm) δ 12.83 (br s, 1H), 4.92 (s, 1H), 4.14 (d, J=8 Hz, 1H), 4.07 (d, J=8 Hz, 1H), 1.41 (s, 9H), 0.88 (s, 9H).

Compound 60 (D-Serine-2-d):

A mixture of Compound 50 (500 g, 1.8 mol, 1.0 equiv), ethanol (1.0 L) and aqueous 2.2N HCl (1.0 L, 2.2 mol, 1.2 equiv) was stirred at 65° C. for 4 hours then was cooled to 15° C. The resulting mixture was adjusted to pH 5 with triethylamine (286 mL) the diluted with ethanol (3.0 L). The resulting slurry was stirred at 20° C. for 60 minutes then filtered. The filter cake was then rinsed with a 9:1 ethanol/water solution (2.0 L) and dried under vacuum. The resulting white solid was transferred to a 1 L flask and water (504 mL) was added. After stirring at 20° C. for 1 hour the resulting aqueous solution was charged through an in-line filter to a 40° C. solution of ethanol (2000 mL) over 20 minutes. The resulting suspension was stirred at 40° C. for 1 hour then was cooled to 20° C. over 30 minutes and filtered. The filter cake was rinsed with ethanol (670 mL) and dried under vacuum to afford compound 60 (163 g, 84% yield, >99% D) as a white crystalline solid. 400 MHz 1H NMR (0.7M NaOD/D$_2$O, ppm) δ 3.68 (d, J=12 Hz, 1H), 3.59 (d, J=12 Hz, 1H).

Example 3: Alternative Method of Preparing Compound 50

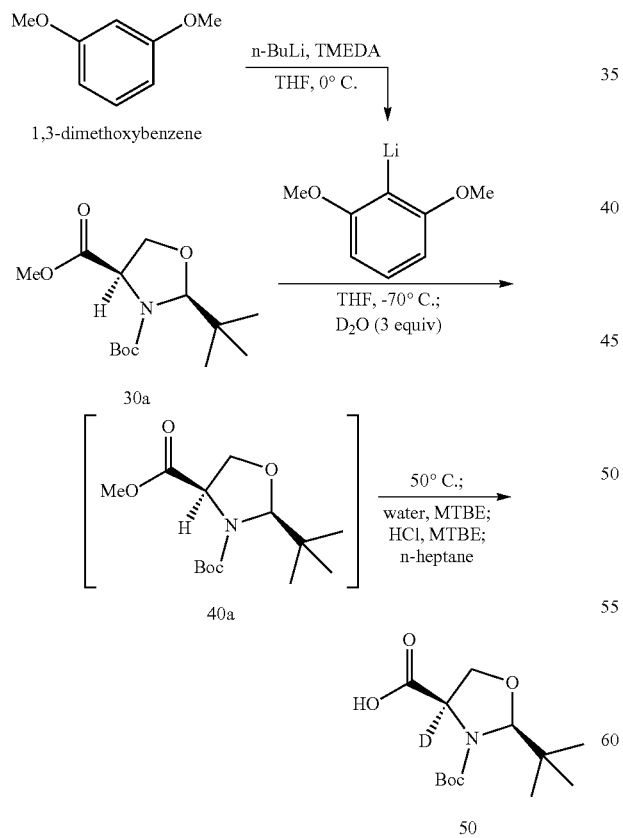

1,3-Dimethoxybenzene (57.9 mL, 0.442 mol, 1.4 equiv) and TMEDA (6.77 mL, 0.045 mol, 0.14 equiv) were added to THF (289 mL) and the resulting solution was cooled to 0° C. A 2.5 M solution of n-butyllithium in hexanes (164 mL, 0.410 mol, 1.3 equiv) was then added at such a rate to maintain the reaction temperature below 5° C. After stirring at 0-5° C. for 60 minutes, a clear yellow solution or 2,6-dimethoxyphenyllithium was obtained. To a separate flask was added Compound 30a (90.7 g, 0.316 mol) and THF (400 mL) and the resulting clear solution was cooled to −80° C. The solution of 2,6-dimethoxyphenyllithium was then transferred to the solution of Compound 30a at such a rate to maintain the reaction temperature below −65° C. Residual 2,6-dimethoxyphenyllithium was then rinsed into the reaction with additional THF (28.9 mL) to afford a pale-orange hazy solution. After stirring at −75° C. for 15 minutes, a solution of D$_2$O (17.1 mL, 0.95 mol, 3.0 equiv) in THF (17.1 mL) was added at such a rate to maintain the reaction temperature below −65° C. Once the addition was complete, the reaction was warmed to 50° C. and stirred at this temperature for 16 hours then cooled to 20° C. Water (454 mL) was then added and the resulting mixture was washed with MTBE (2×454 mL). The organic phases were discarded and the aqueous phase was acidified to pH 3.3 with 1.0 N HCl (446 mL). The aqueous solution was then extracted with MTBE (2×454 mL) and the aqueous phase was discarded. The organic phases were combined and concentrated in vacuo to dryness. n-Heptane (546 mL) was then charged and the resulting white suspension was stirred at reflux (98° C.) until complete dissolution was achieved then was cooled to 20° C. and filtered. The filter cake was washed with n-heptane (200 mL) then dried by vacuum at 20° C. to afford Compound 50 (76.1 g, 87% yield, >99% D) as a white crystalline solid. 400 MHz 1H NMR (d$_6$-DMSO, ppm) δ 12.83 (br s, 1H), 4.92 (s, 1H), 4.14 (d, J=8 Hz, 1H), 4.07 (d, J=8 Hz, 1H), 1.41 (s, 9H), 0.88 (s, 9H).

The invention claimed is:

1. A method for preparing D-serine-2-d,

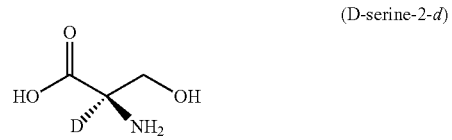

the method comprising:
contacting a compound of Formula E;

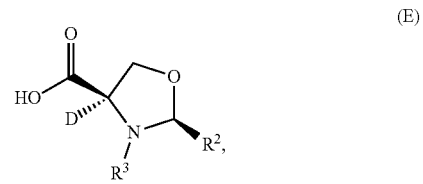

wherein
R$^2$ is C$_1$-C$_6$alkyl, C$_3$-C$_6$cycloalkyl, or aryl; and
R$^3$ is H, D, or a protecting group,
with acid under conditions suitable for opening of the oxazolidine ring;
and optionally removing the R$^3$ protecting group in the same or in a separate step as the contacting step, such that D-serine-2-d is formed;
wherein the D-serine-2-d has a deuterium incorporation of at least 90% at the position specified as deuterium.

2. The method of claim 1, wherein in the compound of Formula E, $R^2$ is $C_1$-$C_6$alkyl.

3. The method of claim 1 or claim 2, wherein $R^2$ is isopropyl or t-butyl.

4. The method of claim 1, wherein $R^3$ is a protecting group.

5. The method of claim 1, wherein $R^3$ is a protecting group selected from —C(O)H, —C(O)—X—$C_1$-$C_6$alkyl, —C(O)—X—$C_3$-$C_6$cycloalkyl, —C(O)—X—$CH_2$-aryl, —C(O)—X-aryl, and —$CH_2$-aryl, wherein X is absent, O, NH, or S.

6. The method of claim 1, wherein the compound of Formula E is selected from the group consisting of:

(50)

(50c)

and (50d)

and wherein the contacting step comprises removing the protecting group in the same step as the opening of the oxazolidine ring.

7. The method of claim 1, wherein the method further comprises, prior to the step of contacting the compound of Formula E to conditions suitable for removal of the amine-protecting group $R^3$ and opening of the oxazolidine ring, the steps of:

(i) contacting a compound of Formula B:

(B)

wherein
$R^1$ is H, $C_1$-$C_6$alkyl, $C_3$-$C_6$cycloalkyl, —$CH_2$-aryl, or aryl;
$R^2$ is $C_1$-$C_6$alkyl, $C_3$-$C_6$cycloalkyl, or aryl; and
$R^3$ is H, D, or a protecting group,
with a base to form a first reaction mixture;

(ii) contacting the first reaction mixture with a deuterium source to form a second reaction mixture under conditions such that the compound of structure (D) is formed:

(D)

wherein $R^1$, $R^2$ and $R^3$ are as defined for the compound of Formula (B); and (iii) contacting the second reaction mixture with a base to form the compound of Formula E.

8. The method of claim 6, wherein the acid is HCl.

9. The method of claim 7, wherein the compound of Formula E is compound 50:

(50)

10. The method of claim 7, wherein the step of contacting the second reaction mixture with a base comprises contacting the second reaction mixture with 1-10 equivalents of lithium deuteroxide.

11. A compound represented by the structure (D):

(D)

wherein
$R^1$ is H, $C_1$-$C_6$alkyl, $C_3$-$C_6$cycloalkyl, —$CH_2$-aryl, or aryl;
$R^2$ is $C_1$-$C_6$alkyl, $C_3$-$C_6$cycloalkyl, or aryl; and
$R^3$ is H, D, or a protecting group;
wherein the compound has a deuterium incorporation of at least 90% at the position specified as deuterium.

12. The compound of claim 11, wherein $R^3$ is H.

13. The compound of claim 11, wherein $R^3$ is a protecting group selected from the group consisting of —C(O)H, —C(O)—X—$C_1$-$C_6$alkyl, —C(O)—X—$C_3$-$C_6$cycloalkyl, —C(O)—X—$CH_2$-aryl, —C(O)—X-aryl, —$CH_2$-aryl, —S(O)$_2$$C_1$-$C_6$alkyl, and S(O)$_2$-aryl, wherein X is absent, O or $NR^4$, wherein $R^4$ is H or $C_1$-$C_6$alkyl.

14. The compound of claim 13, wherein $R^3$ is a protecting group selected from the group consisting of —C(O)H, —C(O)—X—$C_1$-$C_6$alkyl, —C(O)—X—$C_3$-$C_6$cycloalkyl, —C(O)—X—$CH_2$-aryl, —C(O)—X-aryl, —S(O)$_2$$C_1$-$C_6$alkyl, and S(O)$_2$-aryl, wherein X is absent, O or $NR^4$, wherein $R^4$ is $C_1$-$C_6$alkyl.

15. A method for preparing a compound represented by the structure (E):

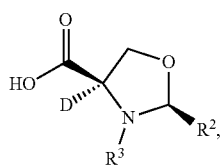

wherein
R² is C₁-C₆alkyl, C₃-C₆cycloalkyl, or aryl; and
R³ is H, D, —C(O)H, —C(O)—X—C₁-C₆alkyl, —C(O)—X—C₃-C₆cycloalkyl, —C(O)—X—CH₂-aryl, —C(O)—X-aryl, or —CH₂-aryl, wherein X is absent, O, NH, or S;
wherein the compound has a deuterium incorporation of at least 90% at the position specified as deuterium,
the method comprising the steps of:
(i) contacting a compound represented by structure (B)

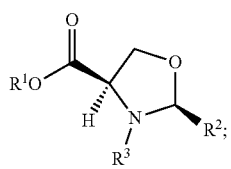

in which R¹ is H or C₁-C₆alkyl,
R² and R³ are as defined for the compound of Formula (E)
with a base to form a reaction mixture;
(ii) contacting the reaction mixture with a deuterium source;
under conditions such that the compound represented by structure (D) is formed:

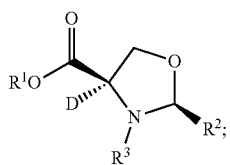

in which R¹ is H or C₁-C₆alkyl,
R² and R³ are as defined for the compound of Formula (E)
and
(iii) reacting the compound of structure (D) with a base to form the compound of structure (E).

16. The method of claim 15, wherein the base of step (i) is selected from mesityllithium, 2,6-dimethoxyphenyllithium, 2,4,6-trimethoxyphenyllithium, tolyllithium, t-butyllithium, phenyllithium, lithium hexamethyldisilazide (LHMDS), trityllithium, phenyl sodium and tritylsodium.

17. The method of claim 15, wherein the deuterium source is D₂O.

18. The method of claim 15, wherein the step of contacting the reaction mixture with a deuterium source comprises contacting the reaction mixture with 1-10 equivalents of the deuterium source.

19. The method of claim 15, wherein,
the compound represented by the structure (E) is compound 50:

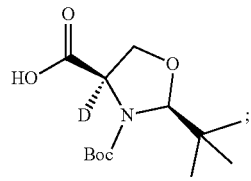

the compound represented by structure (B) is compound 30a:

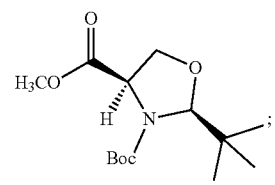

and
the base of step (i) is selected from mesityllithium, 2,6-dimethoxyphenyllithium and 2,4,6-trimethoxyphenyllithium.

20. The method of claim 15, wherein,
the compound represented by the structure (E) is compound 50c:

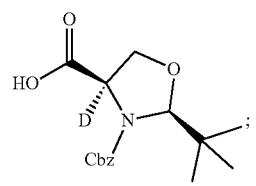

the compound represented by structure (B) is compound 30e:

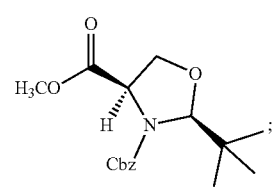

and
the base of step (i) is selected from mesityllithium, 2,6-dimethoxyphenyllithium and 2,4,6-trimethoxyphenyllithium.

21. The method of claim 15, wherein,
the compound represented by the structure (E) is compound 50d:
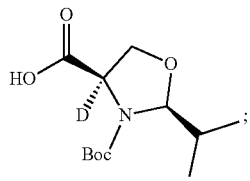
(50d)
the compound represented by structure (B) is compound 30d:
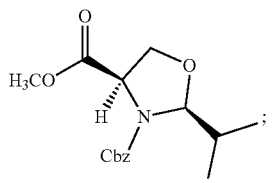
(30d)
and
the base of step (i) is selected from mesityllithium, 2,6-dimethoxyphenyllithium and 2,4,6-trimethoxyphenyllithium.
* * * * *